United States Patent
Um et al.

(10) Patent No.: US 7,842,498 B2
(45) Date of Patent: Nov. 30, 2010

(54) HYDROPHOBIC SURFACE CHIP

(75) Inventors: Pil-Je Um, Pittsburg, CA (US); Christopher A. Pohl, Union City, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 199 days.

(21) Appl. No.: 10/289,185

(22) Filed: Nov. 5, 2002

(65) Prior Publication Data

US 2003/0124371 A1    Jul. 3, 2003

Related U.S. Application Data

(60) Provisional application No. 60/350,110, filed on Nov. 8, 2001.

(51) Int. Cl.
*C12M 3/00* (2006.01)
*C12M 1/34* (2006.01)
*C12M 1/00* (2006.01)
*C12Q 1/68* (2006.01)
*G01N 24/00* (2006.01)

(52) U.S. Cl. ............ 435/287.2; 435/6; 435/283.1; 436/173

(58) Field of Classification Search .......... None
See application file for complete search history.

(56) References Cited

U.S. PATENT DOCUMENTS

| | | | |
|---|---|---|---|
| 4,912,032 A | | 3/1990 | Hoffman et al. |
| 5,399,591 A | * | 3/1995 | Smith et al. ............. 521/53 |
| 5,714,538 A | * | 2/1998 | Beach et al. ............. 524/504 |
| 5,719,060 A | | 2/1998 | Hutchens et al. |
| 5,770,721 A | | 6/1998 | Ershov et al. |
| 5,856,416 A | * | 1/1999 | Bachmann et al. ..... 526/238.23 |
| 5,919,712 A | | 7/1999 | Herron et al. |
| 5,986,043 A | * | 11/1999 | Hubbell et al. ............. 528/354 |
| 6,143,499 A | * | 11/2000 | Mirzabekov et al. ........... 435/6 |
| 6,174,683 B1 | | 1/2001 | Hahn et al. |
| 6,225,047 B1 | | 5/2001 | Hutchens et al. |
| 6,342,244 B1 | * | 1/2002 | Zalipsky ................. 424/450 |
| 6,579,719 B1 | | 6/2003 | Hutchens et al. |
| 6,897,072 B1 | * | 5/2005 | Rich et al. ................. 436/173 |
| 2003/0032043 A1 | | 2/2003 | Pohl et al. |
| 2003/0148979 A1 | * | 8/2003 | Sosnowski et al. ........... 514/44 |

FOREIGN PATENT DOCUMENTS

| | | |
|---|---|---|
| EP | 0 900 809 A1 * | 3/1999 |
| EP | 1 041 053 A1 * | 10/2000 |
| GB | 2348879 A * | 10/2000 |
| WO | WO 00/34804 A1 | 6/2000 |
| WO | WO 00/66265 A2 | 11/2000 |
| WO | WO 03/079402 A2 | 9/2003 |

OTHER PUBLICATIONS

Alberts et al, Molecular Biology of the Cell, 3rd ed., 1994, Garland, New York.*

(Continued)

*Primary Examiner*—Robert T. Crow
(74) *Attorney, Agent, or Firm*—Morgan & Lewis & Bockius, LLP

(57) ABSTRACT

The invention provides a water-swellable hydrophobic hydrogel and analytical devices incorporating the hydrogel of the invention. Also provided are methods of using the hydrogel to prepare the analytical devices and methods of using the analytical devices to detect, quantitate and discriminate between analytes in a sample. Moreover, the invention provides kits that include components of a hydrogel and instructions for making a chip with a hydrophobic surface.

11 Claims, 9 Drawing Sheets

OTHER PUBLICATIONS

Giebel et al, Biophys. J., 1999, 76, 509-516.*
Kounonen et al, J. Biomed. Mat. Res., 1992, 26, 1325-1341.*
Stratagene Catalog, 1998.*
Promega Catalog, 1993/1994.*
Webster, Webster's Third New International Dictionary, Miriam-Webster Inc., USA, p. 1756 (1986).*
The defintion of "disperse" provided by the online dictionary at Merriam-Webster.com.*
Zhou et al, Polymer, vol. 34, No. 24, pp. 5128-5133, 1993.*
The definition of "disperse" provided by the online dictionary at werriam-webster.com [retrieved on Nov. 26, 2008]. Retrieved from the Internet: <URL: www.merriam-webstercom/dictionary/disperse>.*
Michael R. Buchmeiser, "New synthetic ways for preparation of high-performance liquid chromatography supports", *Journal of Chromatography*, vol. 918(2), May 25, 2001, pp. 233-266.
Jay F Künzler, "Silcone Hydrogels for Contact Lens Application", *Trends in Polymer Science*, vol. 4(2), Feb. 1, 1996, pp. 52-59.
J. Varshosaz, et al., Drug diffusion mechanism through pH-sensitive hydrophobic/polyelectrolyte hydrogel membranes, *European Journal of Pharmaceutics and Biopharmaceutics*, vol. 51(3), May (2001), pp. 235-240.

* cited by examiner

HYDROPHOBIC SURFACE CHIP

CROSS-REFERENCES TO RELATED APPLICATIONS

This is a non-provisional filing of U.S. Provisional Patent Application No. 60/350,110, filed on Nov. 8, 2001, the disclosure of which is incorporated herein by reference in its entirety for all purposes.

BACKGROUND OF THE INVENTION

Bioassays are used to probe for the presence and/or the quantity of a target material in a biological sample. In surface based assays, the target amount is quantified by capturing it on a solid support and then detecting it. One example of a surface-based assay is a DNA microarray. The use of DNA microarrays has become widely adopted in the study of gene expression and genotyping due to the ability to monitor large numbers of genes simultaneously (Schena et al., *Science* 270: 467-470 (1995); Pollack et al., *Nat. Genet.* 23:41-46 (1999)). More than 100,000 different probe sequences can be bound to distinct spatial locations across the microarray surface, each spot corresponding to a single gene (Schena et al., *Tibtech* 16:301-306 (1998)). When a fluorescent-labeled DNA target sample is placed over the surface of the array, individual DNA strands hybridize to complementary strands within each array spot. The level of fluorescence detected quantifies the number of copies bound to the array surface and therefore the relative presence of each gene, while the location of each spot determines the gene identity. Using arrays, it is theoretically possible to simultaneously monitor the expression of all genes in the human genome. This is an extremely powerful technique, with applications spanning all areas of genetics. (For some examples, see the Chipping Forecast supplement to *Nature Genetics* 21 (1999)). Arrays can also be fabricated using other binding moieties such as antibodies, proteins, haptens or aptamers, in order to facilitate a wide variety of bioassays in array format.

Other surface-based assays include microtitre plate-based ELISAs in which the bottom of each well is coated with a different antibody. A protein sample is then added to each well along with a fluorescent-labeled secondary antibody for each protein. Target proteins are captured on the surface of each well and secondarily labeled with a fluorophore. The fluorescence intensity at the bottom of each well is used to quantify the amount of each target molecule in the sample. Similarly, antibodies or DNA can be bound to a microsphere such as a polymer bead and assayed as described above. Once again, each of these assay formats is amenable for use with a plurality of binding moieties as described for arrays.

Other bioassays are of use in the fields of proteomics, and the like. For example, cell function, both normal and pathologic, depends, in part, on the genes expressed by the cell (i.e., gene function). Gene expression has both qualitative and quantitative aspects. That is, cells may differ both in terms of the particular genes expressed and in terms of the relative level of expression of the same gene. Differential gene expression is manifested, for example, by differences in the expression of proteins encoded by the gene, or in post-translational modifications of expressed proteins. For example, proteins can be decorated with carbohydrates or phosphate groups, or they can be processed through peptide cleavage. Thus, at the biochemical level, a cell represents a complex mixture of organic biomolecules.

One goal of functional genomics ("proteomics") is the identification and characterization of organic biomolecules that are differentially expressed between cell types. By comparing expression, one can identify molecules that may be responsible for a particular pathologic activity of a cell. For example, identifying a protein that is expressed in cancer cells but not in normal cells is useful for diagnosis and, ultimately, for drug discovery and treatment of the pathology. Upon completion of the Human Genome Project, all the human genes will have been cloned, sequenced and organized in databases. In this "post-genome" world, the ability to identify differentially expressed proteins will lead, in turn, to the identification of the genes that encode them. Thus, the power of genetics can be brought to bear on problems of cell function.

Differential chemical analyses of gene expression and function require tools that can resolve the complex mixture of molecules in a cell, quantify them and identify them, even when present in trace amounts. The current tools of analytical chemistry for this purpose are presently limited in each of these areas. One popular biomolecular separation method is gel electrophoresis. Frequently, a first separation of proteins by isoelectric focusing in a gel is coupled with a second separation by sodium dodecyl sulfate-polyacrylamide gel electrophoresis (SDS-PAGE). The result is a map that resolves proteins according to the dimensions of isoelectric point (net charge) and size (i.e., mass). Although useful, this method is limited in several ways. First, the method provides information only about two characteristics of a biomolecule-mass and isoelectric point ("pI"). Second, the resolution power in each of the dimensions is limited by the resolving power of the gel. For example, molecules whose mass differ by less than about 5% or less than about 0.5 pI are often difficult to resolve. Third, gels have limited loading capacity, and thus limited sensitivity; one often cannot detect biomolecules that are expressed in small quantities. Fourth, small proteins and peptides with a molecular mass below about 10-20 kDa are not observed.

The use of functionalized chips is replacing gels as the method of choice for bioassays. Efforts to improved the sensitivity of assays have resulted in a number of chip designs. For example, a specific binding assay device, which comprises multilayer analytical materials is known (see, for example, EP 51183, EP 66648, DE 3227474 and EP 236768). other multilayer chips are set forth in U.S. Pat. Nos. 4,839,278 and 4,356,149.

An effective chip for bioassay applications must have adequate capacity to immobilize a sufficient amount of an analyte from relevant samples in order to provide a suitable signal when subjected to detection (e.g., mass spectroscopy analysis). Suitable chips must also provide a highly reproducible surface in order to be gainfully applied to profiling experiments, particularly in assay formats in which the sample and the control must be analyzed on separate adjacent chip surfaces. Chips that are not based on a highly reproducible surface chemistry result in significant errors when undertaking assays (e.g., profiling comparisons).

In general, there has been difficulty in producing chips that include and adsorbent layer, which is both water-swellable and sufficiently hydrophobic to interact with an immobilize an analyte. Polymeric hydrogels have long been recognized to swell in water, and they have been utilized successfully in certain chip formats.

There presently is a need to develop chips that are capable of immobilizing small amounts of analyte and analytes that are only weakly immobilized by the adsorbent layers of presently available chip formats. A promising approach to achieving enhanced immobilization of analytes by an adsorbent film consists of varying the hydrophobicity of a water-swellable polymer, such as a hydrogel, used as the adsorbent layer.

Water-swellable hydrogels based on repeating hydrophobic and hydrophilic groups are generally known in the art. For example, Reich et al. (U.S. Pat. No. 5,962,620) describe a hydrogel that is assembled from an alkylene glycol, a hydrophobic diol, a hydrophilic diol and a diisocyanate and water. The hydrogel is a polyuretheane having high slip, Shore A Hardness values, wet tensile strength and tear strength. The polyurethane is disclosed as being of use in catheters, shaving products, synthetic valves, veins and arteries, stents, ports, shunts and coatings.

Shah (U.S. Pat. No. 4,693887) has described a hydrogel that includes separated hydrophilic and hydrophobic microphases for use as a drug delivery vehicle. The hydrogel compositions are blends of either a water-soluble homopolymer of N-vinyl lactam, or a water-soluble copolymer of an N-vinyl lactam with 1 to 90 mole percent of copolymerizable monomer containing ethylenic unsaturation, and a water-insoluble copolymer. The polymers are not cross-linked.

Pathak et al. (U.S. Pat. No. 6,201,065) disclose gel-forming macromers that include at least four polymeric blocks. At least two of the polymeric blocks are hydrophobic and at least one is hydrophilic. The gels include a cross-linker.

Good and Mueller (U.S. Pat. No. 4,277,582) disclose a two-component hydrogel system composed of a macromer, such as polyalkylene oxide, having reactive terminal vinyl groups, crosslinked polymers and copolymers of hydrophilic monomers, such as hydroxyethyl methacrylate, vinyl pyrrolidone, etc. The authors have described the use of these two-component hydrogels as carriers for controlled delivery of pharmaceutically active drugs or agents.

Rich et al. (WO 00/66265, Nov. 9, 2000) disclose probes for a gas phase ion spectrometer. The probes comprise a substrate having a surface and a hydrogel material on the surface. The hydrogel material is crosslinked and comprises binding functionalities for binding with an analyte detectable by the gas phase ion spectrometer.

There presently is a tremendous need for chips that provide reproducible results from assay to assay, which are easy to use, and provide quantitative data in multi-analyte systems. Moreover, to become widely accepted, the chips should be inexpensive to make, and to use for the detection of analytes. The availability of a chip having the above-described characteristics would significantly affect research, individual point of care situations (doctor's office, emergency room, out in the field, etc.), and high throughput testing applications. The present invention provides chips having these and other desirable characteristics

BRIEF SUMMARY OF THE INVENTION

It has now been discovered that water-swellable hydrophobic hydrogels can be assembled from a combination of a hydrophobic monomer, a hydrophilic monomer and cross-linking agent, or from a monomer comprising both hydrophobic and hydrophilic functionalities and a cross-linking agent. The hydrophobic hydrogel of the invention is particularly useful as an adsorbent layer on a substrate of a chip used for an analytical method. The hydrophobic moieties are useful for immobilizing an analyte, e.g., a polypeptide, onto the adsorbent layer. The hydrophilic moieties allow the hydrogel to swell in water, which in turn increases the capacity of the hydrogel to immobilize an analyte by allowing the analyte access to more of the surface area of the hydrogel. Moreover, as the hydrogel includes a combination of hydrophobic moieties and hydrophilic moieties, the degree of hydrophobicity (avidity for analyte) and water-swellability (capacity for analyte) can be engineered by varying the ratio of the hydrophilic moieties and hydrophobic moieties in the hydrogel.

Thus, in a first aspect, the invention provides an adsorbent chip. The chip includes a substrate, which has a surface; and an adsorbent layer attached to the surface. The adsorbent layer includes a hydrogel made of hydrophobic moieties and hydrophilic moieties. The hydrogel is water-swellable and and binds an analyte in a salt-independent hydrophobic attraction.

In a second aspect, the present invention provides a method for making an adsorbent chip. The method includes, covalently coupling an anchor reagent to a substrate surface via complementary reactive groups on said surface and said anchor reagent. The anchor reagent includes within its structure a locus for attaching a hydrogel adsorbent layer. The locus is contacted with a polymerizable hydrophobic monomer, a polymerizable hydrophilic monomer and a polymerizable cross-linker. A polymerization reaction is initiated, which results in the copolymerization of the polymerizable hydrophobic monomer, the polymerizable hydrophilic monomer, the locus, and the polymerizable cross-linker. At the completion of the reaction, an adsorbent layer is formed that includes a copolymeric hydrogel of the invention immobilized onto the chip surface via the The nature of the substrate depends upon the intended use of the adsorbent biochip. If the chip is to be used in linear time-of-flight mass spectrometry, the substrate preferably includes a conductive material, such as a metal. If the biochip is to be used in mass spectrometry involving orthogonal extraction, the substrate preferably includes a non-conductive material. If the biochip is to be used in another detection method, such as fluorescence detection at the biochip surface, suitable materials, such as plastics or glass can be used. The substrate typically will have functional groups through which the intermediate layer can be attached. For example, an aluminum chip can be covered with silicon dioxide. Other metals, such as anodized aluminum already have surfaces with functional groups. Alternatively, the substrate may be composed of plastic in which case the functional groups may already be present as an integral surface component or the surface may be derivatized, making use of methods well-known to those skilled in the art.

In another aspect, this invention provides a method for detecting an analyte in a sample comprising contacting the analyte with an adsorbent biochip of this invention to allow capture of the analyte and detecting capture of the analyte by the adsorbent chip. In certain embodiments, the analyte is a biomolecule, such as a polypeptide, a polynucleotide, a carbohydrate or a lipid. In other embodiments, the analyte is an organic molecule such as a drug candidate. In certain embodiments, the analyte is detected by mass spectrometry, in particular by laser desorption/ionization mass spectrometry. In such methods, when the analyte is a biomolecule, the method preferably comprises applying a matrix to the captured analyte before detection. In other embodiments the analyte is labeled, e.g., fluorescently, and is detected on the chip by a detector of the label, e.g., a fluorescence detector such as a CCD array. In certain embodiments the method involves profiling a certain class of analytes (e.g., biomolecules) in a sample by applying the sample to one or addressable locations and detecting analytes captured at the addressable location or locations.

In a further aspect, the present invention provides a kit. In an exemplary embodiment, the kit includes a substrate and one or more containers charged with a monomer or a cross-linker. The kit also optionally includes instructions for preparing a cross-linked hydrogel and for assembling an adsorbent chip of the invention by combining the substrate and the cross-linked hydrogel.

Other aspects, objects and advantages of the present invention will be apparent from the detailed description that follows.

DETAILED DESCRIPTION OF THE INVENTION AND THE PREFERRED EMBODIMENTS

Abbreviations

Figure 1:
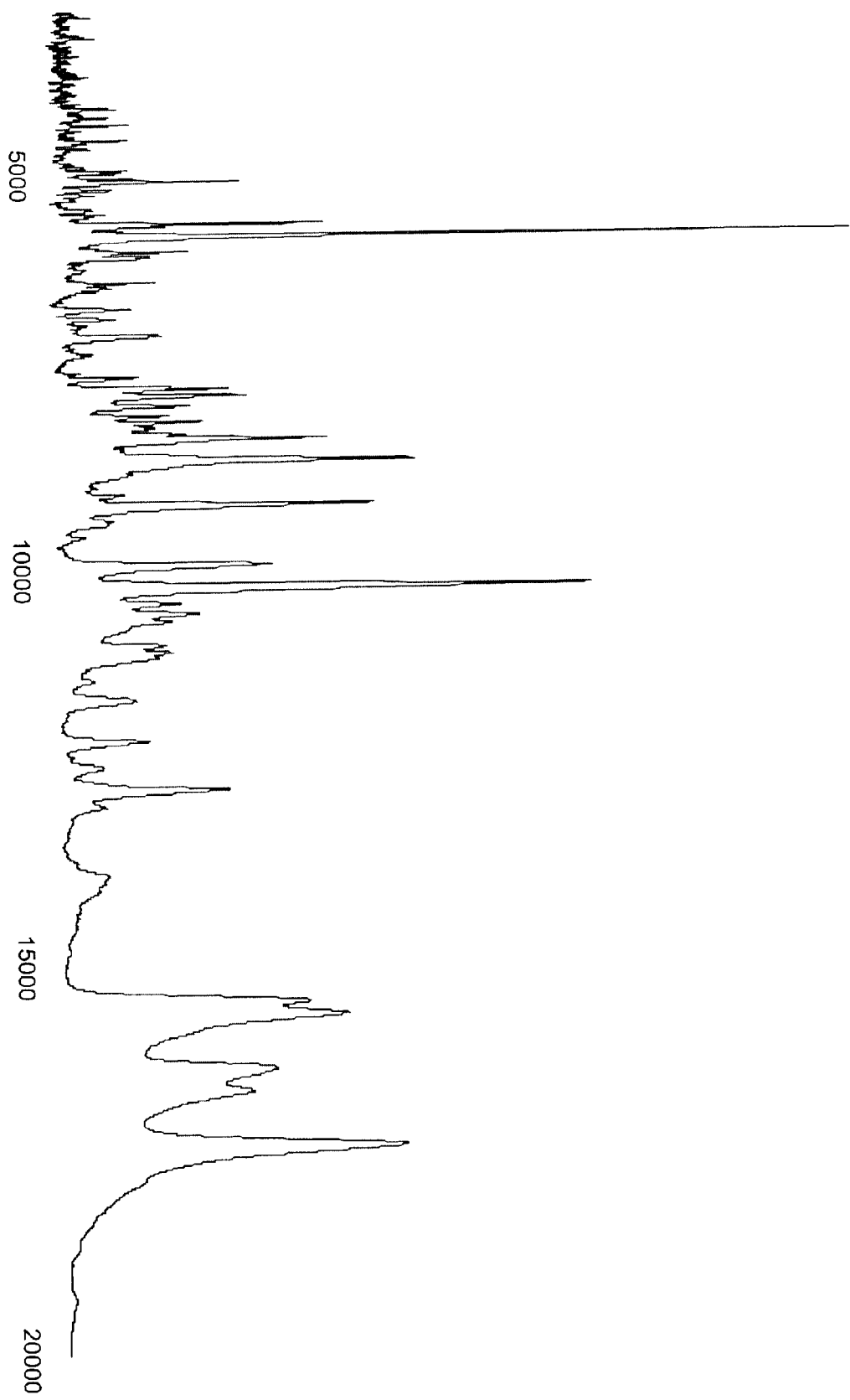
FIG. 1 is a mass spectrum of an extract of rat brain adsorbed onto a chip of the invention in 1% aqueous trifluoroacetic acid.

"H4," as used herein refers to a linear $C_{16}$ polymer that is not appreciably water-swellable, and more particularly, a chip incorporating the $C_{16}$ polymer.

"H50," and "C9" are used interchangeably to refer to a hydrogel of the invention, and more particularly to a chip incorporating a hydrogel of the invention.

Definitions

Where substituent groups are specified by their conventional chemical formulae, written from left to right, they equally encompass the chemically identical substituents which would result from writing the structure from right to left, e.g., —$CH_2O$— is intended to also recite —$OCH_2$—; —$NHS(O)_2$— is also intended to represent. —$S(O)_2HN$—, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents both —$C(O)_2$R'— and —R'$C(O)_2$—.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O) NR"R'", —NR"C(O)$_2$R', —NR—C(NR'R"R'")=NR"", —NR—C(NR'R")=NR'", —S(O)R', —S(O)$_2$R', —S(O)$_2$ NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Each of the above terms are meant to include both substituted and unsubstituted forms of the indicated radical.

As used herein, the term "heteroatom" is meant to include oxygen (O), nitrogen (N), sulfur (S) and silicon (Si).

"Target," and "target species, as utilized herein refers to the species of interest in an assay mixture. Exemplary targets include, but are not limited to cells and portions thereof, enzymes, antibodies and other biomolecules, drugs, pesticides, herbicides, agents of war and other bioactive agents.

The term "substance to be assayed" as used herein means a substance, which is detected qualitatively or quantitatively by the process or the device of the present invention. Examples of such substances include antibodies, antibody fragments, antigens, polypeptides, glycoproteins, polysaccharides, complex glycolipids, nucleic acids, effector molecules, receptor molecules, enzymes, inhibitors and the like.

More illustratively, such substances include, but are not limited to, tumor markers such as α-fetoprotein, carcinoembryonic antigen (CEA), CA 125, CA 19-9 and the like; various proteins, glycoproteins and complex glycolipids such as $β_2$-microglobulin ($β_2$ m), ferritin and the like; various hormones such as estradiol ($E_2$), estriol ($E_3$), human chorionic gonadotropin (hCG), luteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the target and other components. The other components are, for example, diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

The term "drug" or "pharmaceutical agent," refers to bioactive compounds that cause an effect in a biological organism. Drugs used as affinity moieties or targets can be neutral or in their salt forms. Moreover, the compounds can be used in the present method in a prodrug form. Prodrugs are those compounds that readily undergo chemical changes under physiological conditions to provide the compounds of interest in the present invention.

The term "binding functionality" as used herein means a moiety, which has an affinity for a certain substance such as a "substance to be assayed," that is, a moiety capable of interacting with a specific substance to immobilize it on the chip of the invention. Binding functionalities of use in practicing the present invention are generally. Chromatographic binding functionalities bind substances via charge-charge, hydrophilic-hydrophilic, hydrophobic-hydrophobic, van der Waals interactions and combinations thereof. Biospecific binding functionalities generally involve complementary 3-dimensional structures involving one or more of the above interactions.

"Hydrogel" refers to a water-insoluble and water-swellable cross-linked polymer that is capable of absorbing at least 10 times, preferably at least 100 times, its own weight of a liquid.

The term "detection means" as used herein refers to detecting a signal produced by the immobilization of the substance to be assayed onto the binding layer by visual judgment or by using an appropriate external measuring instrument depending on the signal properties.

The term "attached," as used herein encompasses interaction including, but not limited to, covalent bonding, ionic bonding, chemisorption, physisorption and combinations thereof.

The term "independently selected" is used herein to indicate that the groups so described can be identical or different.

The term "biomolecule" or "bioorganic molecule" refers to an organic molecule typically made by living organisms. This includes, for example, molecules comprising nucleotides, amino acids, sugars, fatty acids, steroids, nucleic acids, polypeptides, peptides, peptide fragments, carbohydrates, lipids, and combinations of these (e.g., glycoproteins, ribonucleoproteins, lipoproteins, or the like).

The term "biological material" refers to any material derived from an organism, organ, tissue, cell or virus. This includes biological fluids such as saliva, blood, urine, lymphatic fluid, prostatic or seminal fluid, milk, etc., as well as extracts of any of these, e.g., cell extracts, cell culture media, fractionated samples, or the like.

As used herein, a gel exhibits "salt-independent hydrophobic attraction" if it can bind a certain amount of protein under certain conditions. More specifically, when contacted with at least two gel volumes of 5 mg/ml of bovine ribonuclease A in 1% trifluoroacetic acid in water and washed with 1% trifluoroacetic acid in water, a gel of this invention is capable of binding at least 0.1 mg of bovine ribonuclease A per milliliter of gel, more preferably, at least 0.5 mgs/ml, more preferably at least 1 mg/ml, most preferably at least 3 mgs/ml. The amount bound is determined by eluting the protein using a solution of 50% acetonitrile in water and determining the amount of protein eluted.

Water-swellable, as used herein, refers to a hydrogel wherein a unit weight of said hydrogel absorbs water in an amount from about 10-times to about 100-times said unit weight.

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter which can be translated into mass-to-charge ratios of gas phase ions. Mass spectrometers generally include an ion source and a mass analyzer. Examples of mass spectrometers are time-of-flight, magnetic sector, quadrapole filter, ion trap, ion cyclotron resonance, electrostatic sector analyzer and hybrids of these. "Mass spectrometry" refers to the use of mass spectrometry to detect gas phase ions.

"Ion source" refers to a sub-assembly of a gas phase ion spectrometer that provides gas phase ions. In one embodiment, the ion source provides ions through a desorption/ ionization process. Such embodiments generally comprise a probe interface that positionally engages probe in an interrogatable relationship to a source of ionizing energy (e.g., a laser desorption/ionization source) and in concurrent communication at atmospheric or subatmospheric pressure with a detector of a gas phase ion spectrometer. The preferred form of ionizing energy is a laser (used in laser desorption/ionization), in particular, nitrogen lasers, Nd-Yag lasers and other pulsed laser sources. Other forms of ionizing energy include fast atoms (used in fast atom bombardment), plasma energy (used in plasma desorption) and primary ions generating secondary ions (used in secondary ion mass spectrometry). Typically, a sample is placed on the surface of a probe, the probe is engaged with the probe interface and the probe surface is struck with the ionizing energy. The energy desorbs analyte molecules from the surface into the gas phase and ionizes them.

"Probe" refers to a device that can be used to introduce ions derived from an analyte into a gas phase ion spectrometer, such as a mass spectrometer. A "probe" will generally comprise a solid substrate (either flexible or rigid) comprising a sample presenting surface on which an analyte is presented to the source of ionizing energy.

"Biochip" refers to a solid substrate having a generally planar surface to which a capture reagent is attached (the capture reagent can be an inorganic, organic, or biologic moiety). Frequently, the surface of the biochip comprises a plurality of addressable locations, each of which location has the capture reagent bound there. In certain embodiments, biochips adapted to function as probes in gas phase ion spectrometry.

Upon capture, analytes can be detected by a variety of detection methods including for example, gas phase ion spectrometry methods, optical methods, electrochemical methods, atomic force microscopy and radio frequency methods. Gas phase ion spectrometry methods are described herein. Of particular interest is the use of SELDI, a mass spectrometric method in which analytes are captured on the surface of a biochip and detected by, e.g., laser desorption/ionization mass spectrometry. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Introduction

Hydrophilic gels in aqueous solution have been widely studied, but many polymers can be cross-linked to form a gel. The three-dimensional network of the gel is stabilized by cross-links. The cross-links are provided by covalent bonds, physical entanglements, crystallites, charge complexes, hydrogen bonding, van der Waal's or hydrophobic interactions. Gels have many technologically important roles in chemical separations, biomedical devices and absorbent products, to name a few areas. The properties that make gels useful include their sorption capacities, swelling kinetics, permeabilities to dissolved solutes, surface properties (e.g., adhesiveness), mechanical characteristics, and optical properties (S. H. Gehrke, p. 85, in Advances in Polymer Science, ed. K. Dusek, Vol. 110 (Springer-Verlag New York 1993).

The present invention provides a cross-linked hydrogel that is both water-swellable and hydrophobic. The hydrophobicity of the hydrogel imparts to it the ability to immobilize analytes, such a polypeptides. The water-swellability of the hydrogel allows an analyte solution to penetrate the three-dimensional structure, resulting in enhanced immobilization of the analyte by the hydrogel. The hydrogel of the invention is of particular use in chips designed for analytical protocols, such as high throughput screening, proteomics, genomics and the like.

In the sections that follow, the hydrophobic hydrogel of the invention is described. The use of the hydrogel in an analytical device, as exemplified by a chip for mass spectrometric analysis is also illustrated. Moreover, methods of using the hydrogel to produce an analytical device are set forth, as are methods of using the analytical device to detect, quantify, or otherwise characterize an analyte are described.

The Hydrogel

The hydrogels of the present invention are unique in that they both are water swellable and capable of binding molecules over a wide range of hydrophobicity under decreased salt conditions. That is, the hydrophobic property of the gel is not salt dependent. This character provides improved performance in SELDI in which the presence of salt interferes with the ability to desorb and detect biomolecular analytes. The salt-independent character of the hydrogels is achieved by using large hydrophobic moieties, for example, moieties having at lest four (e.g., butyl) and more preferably at least eight (e.g., octyl) contiguous carbon or other non-polar atoms. The water swellability is achieved by providing a sufficient amount of hydrophilic moieties in the polymer.

In general, providing larger hydrophobic moieties on a hydrogel decreases water swellability. For example, hydrogels made of isopropyl acrylamide are water swellable and possess small hydrophobic moieties (i.e., an isopropyl group). The hydrophobic binding character of these gels is salt dependent. However, when the isopropyl group is replaced by a larger hydrophobic moiety, e.g., an octyl group, the hydrophobic binding character of the polymer becomes less salt dependent but the gel also loses its water swellability. In the case of PEG acrylate polymer, a suitable ratio to obtain both salt-independent hydrophobic binding and water swellability would be about ten PEG units (hydrophilic) to about two nonyl units (hydrophobic). If one were making a co-polymer of hydrophobic and hydrophilic monomers, the hydrophilic monomers could comprise less than 100% to about 50% of the polymer and the hydrophobic monomers would comprise more than 0% to about 50% by weight. Preferably, the amount of hydrophobic momomers would be about 5% to about 20%, more preferably about 10%. Longer hydrophobic moieties impart greater hydrophobicity. Therefore, a relatively amount of the total mass of the gel can be hydrophilic. Exemplary hydrophilic moieties are derived from monomers that include N-methacryloyl-tris(hydroxymethyl)methylamine, hydroxyethyl acrylamide, hydroxypropyl methacrylamide, N-acrylamido-1-deoxysorbitol, hydroxyethylmethacrylate, hydroxypropylacrylate, hydroxyphenylmethacrylate, poly(ethylene glycol)monomethacrylate, poly(ethylene glycol) dimethacrylate, acrylamide, glycerol monomethacrylate, 2-hydroxypropyl acrylate, 4-hydroxybutyl methacrylate, 2-methacryloxyethyl glucoside, poly(ethyleneglycol) monomethyl ether monomethacrylate, vinyl 4-hydroxybutyl ether, and derivatives thereof.

Presently preferred hydrophobic moieties are derived from acrylamide monomers in which the amine nitrogen of the amide group is substituted with one or more alkyl residues.

Exemplary hydrophobic moieties are derived from monomers selected from N, N-dimethyl acrylamide, N,N-diethyl (meth)acrylamide, N-methyl methacrylamide, N-ethyl methacrylamide, N-propyl acrylamide, N-butyl acrylamide, N-octyl (meth)acrylamide, N-dodecyl methacrylamide, N-octadecyl acrylamide, propyl (meth)acrylate, decyl (meth)acrylate, stearyl (meth)acrylate, octyl-triphenylmethylacrylamide, butyl-triphenylmethylacrylamide, octadedcyl-triphenylmethylacrylamide, phenyl-triphenylmethylacrlamide, benzyl-triphenylmethylacrylamide, and derivatives thereof.

Presently preferred hydrophilic moieties are derived from monomers that include a poly(oxyalkylene) group within their structure. Poly(ethylene glycol)-containing monomers are particularly preferred.

In a particularly preferred embodiment, the hydrophobic and hydrophilic moieties are derived from a single monomer having both hydrophobic and hydrophilic characteristics. Exemplary monomers having the desired characteristics include, but are not limited to compounds according to Formula I:

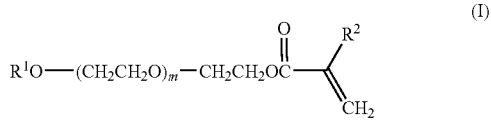

(I)

in which the symbol $R^1$ represents a member selected from substituted or unsubstituted alkyl, substituted or unsubstituted heteroalkyl, and substituted or unsubstituted aryl. The symbol $R^2$ represents a member selected from substituted or unsubstituted alkyl; and m is an integer from 2 to 100. An exemplary monomer according to Formula I is nonylphenoxy-poly(ethylene glycol)methacrylate. In this case, the hydrophilic moieties are represented by ethylene glycol —(CH$_2$CH$_2$O)— and the hydrophobic moieties are represented by $R^1$. As is plain, one can alter the relative hydrophobic character of the molecule by increasing the size of $R^1$, and alter the hydrophilic character by altering the number of ethylene glycol groups.

Essentially any cross-linking agent is of use in preparing the hydrogels of the invention. Useful cross-linking groups include species that cross-link the monomers covalently or ionically. The cross-linking groups in one preferred embodiment are polymerizable through free radical generation by photo-initiation, most preferably in the visible or long wavelength ultraviolet radiation. Exemplary cross-linking agents include unsaturated groups, including vinyl groups, allyl groups, cinnamates, acrylates, diacrylates, oligoacrylates, methacrylates, dimethacrylates, oligomethoacrylates, acrylamides, diacrylamides, oligoacrylamides, or other photopolymerizable groups.

In a preferred embodiment, the cross-linking group has at least two vinyl groups within its structure. Examples of compounds having a plurality of vinyl groups include N,N'-methylene-bis-methacrylamide, poly(ethylene glycol) dimethacrylate, poly(propylene glycol)dimethacrylate, trimethylolpropane trimethacrylate, trimethylolpropane dimethacrylate, glycerine trimethacrylate, glycerine acrylate methacrylate, pentaerythritol tetramethacrylate, dipentaerythritol hexamethacrylate, N,N-diallyl acrylamide, triallyl cyanurate, triallyl isocyanurate, triallyl phosphate, triallylamine, diallyloxy acetate, N-methyl-N-vinyl acrylamide, bis (N-vinyl carboxylic amide), and polymethaliloxy alkanes. Other appropriate crosslinking agents are known to those of skill in the art.

The amount of the cross-linking agent with respect to the hydrophilic and hydrophobic monomers can vary and it is well within the abilities of one of skill in the art to determine an appropriate amount of cross-linking agent to form a hydrogel having desired characteristics. In an exemplary embodiment, the cross-linking agent is used in an amount ranging preferably from 0.0001 weight parts to 10 weight parts, more preferably from 0.001 weight parts to 5 weight parts, most preferably from 0.01 weight parts to 2 weight parts, based on 100 parts by weight of either the hydrophobic or hydrophilic monomer.

When the cross-linking agent is a covalent cross-linker, an exemplary hydrogel of the invention includes a covalent linkage between at least two of the above-recited subunits according to Formula II:

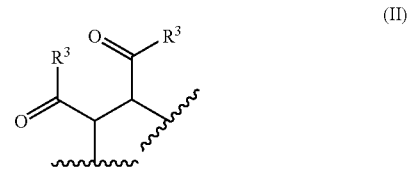

(II)

in which the symbol $R^3$ represents a member selected from $NR^4R^5$ and $C_1$-$C_{16}$ alkyl groups. The symbols $R^4$ and $R^5$ represent members selected from H and $C_1$-$C_{16}$ alkyl groups. The incomplete bonds represent a link to a hydrophobic moiety, a hydrophilic moiety, or another cross-linking moiety.

The mixture of monomers and cross-linking agent are generally polymerized by a known method. The polymerization method is not limited, and various methods can be used. Examples include radical polymerization using a radical polymerization initiator, irradiation-induced polymerization, electron radiation-induced polymerization, and ultraviolet-induced polymerization using a photosensitizer. Among these methods, radical polymerization is more preferred because this method generally leads to near quantitative polymerization of the monomers and cross-linking agents.

When radical polymerization is utilized, there are various polymerization methods, such as aqueous solution polymerization, cast polymerization which is performed within a mold, thin-layer polymerization which is performed on a belt conveyer, polymerization which is performed while making generated hydrogel polymer into small pieces, reversed-phase suspension polymerization, reversed-phase emulsion polymerization, precipitation polymerization, and bulk polymerization.

The aqueous solution polymerization of the unsaturated monomer may be performed either continuously or batch-wise, or may be performed under suction, pressure, or atmospheric pressure. The polymerization is preferably performed in the flow of inactive gas, such as nitrogen, helium, argon, or carbonate gas.

When performing the aqueous solution polymerization, it is preferred to dissolve or disperse a radical polymerization initiator in an aqueous monomer solution in advance. Examples of the radical polymerization initiator include, per-oxides, such as ammonium persulfate, potassium persulfate, sodium persulfate, hydrogen peroxide, benzoyl peroxide, cumene hydroperoxide, and di-t-butyl peroxide; redox initiators formed by combining the above-mentioned peroxides and reducing agents, such as sulfite, bisulfite, thiosulfate, formamidine sulfinic acid, and. ascorbic acid; acrylic acid salts of azo-compound containing an amino group; and azo polymerization initiators, such as hydrochlorides of the azo-compound containing an amino group. These radical polymerization initiators may be used individually, or in combination. When the acrylic acid salt of azo-compound containing an amino group is used as the radical.

The amount of the radical polymerization initiator with respect to the monomers is varied depending on the identity of the monomers and the radical polymerization initiator. In an exemplary embodiment, the amount of the radical polymerization initiator to be used is within a range of preferably from 0.0005 weight parts to 5 weight parts, more preferably from 0.005 weight parts to 2.5 weight parts, based on 100 parts by weight of the monomers.

Although the temperature at the initiation of polymerization varies depending on the type of a radical polymerization initiator used, it is preferably within a, range of from about 0° C. to about 40° C., more preferably from about 10° C. to about 30° C.

The reaction time is not necessarily limited, but is preferably set according to the combination of the monomers, cross-linking agent and radical polymerization initiator, or reaction conditions such as the reaction temperature. In a preferred embodiment, the time range is from about 1 hour to about 1 day.

In certain embodiments, it is desirable to purify the hydrogel of the invention prior to its use. In these embodiments, the hydrogel can be purified in a manner known to those of skill in the art, for example by precipitation with acetone, dialysis or ultrafiltration, particular preference being given to ultrafiltration. This purification operation allows the preparation of hydrogels of the invention, which are free or at least substantially free from reaction products, such as salts, and starting materials, or other non-polymeric constituents.

The preferred method for the purification of the hydrogel, can be carried out in a manner known to those of skill in the art. Ultrafiltration can be performed repeatedly, for example from two to ten times. Alternatively, the ultrafiltration can also be carried out continuously until the desired degree of purity has been achieved. The desired degree of purity can in principle be as great as desired. A suitable measure of the degree of purity is, for example, the sodium chloride content of the solution, which can easily be determined in a manner known, such as gel permeation chromatography (GPC).

The hydrophilicity and hydrophobicity of the gels of the invention can be characterized and quantified by methods well known in the art. As used herein, the term "hydrophilic" is used to refer to surfaces that are wettable by aqueous fluids (e.g., aqueous body fluids) deposited thereon. Hydrophilicity and wettability are typically defined in terms of contact angle and the surface tension of the fluids and solid surfaces involved. This is discussed in detail in the American Chemical Society publication entitled Contact Angle, Wettability and Adhesion, edited by Robert F. Gould (Copyright 1964), which is hereby incorporated herein by reference. A surface is wetted by an aqueous fluid (hydrophilic) when the fluid tends to spread spontaneously across the surface. Conversely, a surface is considered to be "hydrophobic" if the aqueous fluid does not tend to spread spontaneously across the surface.

A gel or surface of a gel is wetted by a fluid (i.e., hydrophilic) when either the contact angle between the fluid and the surface of the gel is less than 90°, or when the fluid tends to spread spontaneously across the surface of the gel. Conversely, a gel or surface is considered to be hydrophobic if the contact angle is greater than 90° and the fluid does not spread spontaneously across the surface of the gel. This is discussed in detail in the American Chemical Society publication entitled Contact Angle, Wettability and Adhesion, edited by Robert F. Gould (Copyright 1964).

Typically, a drop of liquid placed on a surface makes a contact angle with the surface. As the wettability of the surface by the liquid increases, the contact angle decreases. As the wettability of the solid surface by the liquid decreases, the contact angle increases. The liquid-solid contact angle may be determined from techniques known in the art, such as those described in greater detail in Physical Chemistry of Surfaces, Second Edition, by A W Adamson (1967); F E Bartell and H H Zuidema, *J. Am. Chem. Soc.* 58: 1449 (1936), and J J Bikerman, *Ind. Eng. Chem., Anal. Ed.,* 13: 443 (1941), each of which are hereby incorporated herein by reference. More recent publications in this area include Cheng, et al., *Colloids and Surfaces* 43: 151-167 (1990), and Rotenberg, et al., *Journal of Colloid and Interface Science* 93(1): 169-183 (1983), which are also hereby incorporated herein by reference.

The Chip

In a second aspect the present invention provides a chip that includes a substrate having a surface onto which a hydrophobic hydrogel of the invention is immobilized. The invention disclosed herein also includes methods using a chip of the invention for increasing the sensitivity, specificity and dynamic range of assay systems based upon the capture of a target species on the hydrogel. The assays are surface based.

The present invention is further explained and illustrated in the sections which follow, by reference to a representative embodiment using detection by mass spectrometry. The focus on mass spectrometric detection is for purposes of clarity and simplicity of illustration only, and should not be construed as limiting the scope of the present invention or circumscribing the types of methods in which the present invention finds application. Those of skill in the art will recognize that the methods set forth herein are broadly applicable to a number of chip formats and assays using these chips for the detection of a wide range of target moieties.

The components of the chip of the invention are discussed in detail hereinbelow. Those of skill will appreciate that each of the described preferred and alternate embodiments of each of the components are readily combined with the embodiments of other components without limitation.

A. Substrates

In the chip of the invention, the adsorbent film for the target is immobilized on a substrate, either directly or through a flexible linker arm that is intercalated between the substrate and the adsorbent film. The flexible linker is bound to the plane of the substrate surface, or it is bound to a feature of the substrate surface such as a raised (e.g., island) or depressed (e.g., a well, trough, etc.) feature. Substrates that are useful in practicing the present invention can be made of any stable material, or combination of materials. Moreover, useful substrates can be configured to have any convenient geometry or combination of structural features. The substrates can be either rigid or flexible and can be either optically transparent or optically opaque. The substrates can also be electrical insulators, conductors or semiconductors. Further the substrates can be substantially impermeable to liquids, vapors and/or gases or, alternatively, the substrates can be substantially permeable to one or more of these classes of materials.

The materials forming the substrate are utilized in a variety of physical forms such as films, supported powders, glasses, crystals and the like. For example, a substrate can consist of a single inorganic oxide or a composite of more than one inorganic oxide. When more than one component is used to form a substrate, the components can be assembled in, for example a layered structure (i.e., a second oxide deposited on a first oxide) or two or more components can be arranged in a contiguous non-layered structure. Further the substrates can be substantially impermeable to liquids, vapors and/or gases or, alternatively, the substrates can be permeable to one or more of these classes of materials. Moreover, one or more components can be admixed as particles of various sizes and deposited on a support, such as a glass, quartz or metal sheet. Further, a layer of one or more components can be intercalated between two other substrate layers (e.g., metal-oxide-metal, metal-oxide-crystal). Those of skill in the art are able to select an appropriately configured substrate, manufactured from an appropriate material for a particular application.

Exemplary substrate materials include, but are not limited to, inorganic crystals, inorganic glasses, inorganic oxides, metals, organic polymers and combinations thereof. Inorganic glasses and crystals of use in the substrate include, but are not limited to, LiF, NaF, NaCl, KBr, KI, $CaF_2$, $MgF_2$, $HgF_2$, BN, $AsS_3$, ZnS, $Si_3N_4$ and the like. The crystals and glasses can be prepared by art standard techniques. See, for example, Goodman, Crystal Growth Theory and Techniques, Plenum Press, New York 1974. Alternatively, the crystals can be purchased commercially (e.g., Fischer Scientific). Inorganic oxides of use in the present invention include, but are not limited to, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. Metals of use in the substrates of the invention include, but are not limited to, gold, silver, platinum, palladium, nickel, copper and alloys and composites of these metals.

Metals are also of use as substrates in the present invention. The metal can be used as a crystal, a sheet or a powder. In those embodiments in which the metal is layered with another substrate component, the metal can be deposited onto the other substrate by any method known to those of skill in the art including, but not limited to, evaporative deposition, sputtering and electroless deposition.

Any metal that is chemically inert towards the species in a selected analyte sample are useful as a substrate component in the present invention. The metal layers can be either permeable or impermeable to materials such as liquids, solutions, vapors and gases. Presently preferred metals include, but are not limited to, gold, silver, platinum, palladium, nickel, aluminum and copper.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins.

In a preferred embodiment, the substrate material is substantially non-reactive with the target, thus preventing non-specific binding between the substrate and the target or other components of an assay mixture. Methods of coating substrates with materials to prevent non-specific binding are generally known in the art. Exemplary coating agents include, but are not limited to cellulose, bovine serum albumin, and poly(ethyleneglycol). The proper coating agent for a particular application will be apparent to one of skill in the art.

In a further preferred embodiment, the substrate material is substantially non-fluorescent or emits light of a wavelength range that does not interfere with the detection of the target. Exemplary low-background substrates include those disclosed by Cassin et al., U.S. Pat. No. 5,910,287 and Pham et al., U.S. Pat. No. 6,063,338.

The surface of a substrate of use in practicing the present invention can be smooth, rough and/or patterned. The surface can be engineered by the use of mechanical and/or chemical techniques. For example, the surface can be roughened or patterned by rubbing, etching, grooving, stretching, and the oblique deposition of metal films. The substrate can be patterned using techniques such as photolithography (Kleinfield et al., *J. Neurosci.* 8: 4098-120 (1998)), photoetching, chemical etching and microcontact printing (Kumar et al., *Langmuir* 10: 1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm have been layered onto a substrate. See, Xia, Y.; Whitesides, G., *J. Am. Chem. Soc.* 117:3274-75 (1995). Similarly, using photolithography, patterns with features as small as 1 μm have been produced. See, Hickman et al., *J. Vac. Sci. Technol.* 12:607-16 (1994). Patterns which are useful in the present invention include those which comprise features such as wells, enclosures, partitions, recesses, inlets, outlets, channels, troughs, diffraction gratings and the like.

In an exemplary embodiment, the patterning is used to produce a substrate having a plurality of adjacent addressable features, wherein each of the features is seperably identifiable by a detection means. In another exemplary embodiment, an addressable feature does not fluidically communicate with other adjacent features. Thus, an analyte, or other substance, placed in a particular feature remains substantially confined to that feature. In another preferred embodiment, the patterning allows the creation of channels through the device whereby fluids can enter and/or exit the device.

In another exemplary embodiment the anchor reagent (from which the anchor moiety is formed) is printed onto the substrate. The pattern can be printed directly onto the substrate or, alternatively, a "lift off" technique can be utilized. In the lift off technique, a patterned resist is laid onto the substrate, component of the chip is laid down in those areas not covered by the resist and the resist is subsequently removed. Resists are known to those of skill in the art. See, for example, Kleinfield et al., *J. Neurosci.* 8:4098-120 (1998). In some embodiments, following removal of the resist, a second chip component, having a structure different from the first component layer is printed onto the substrate on those areas initially covered by the resist; a process that can be repeated any selected number of times with different components to produce a chip having a desired format.

Using the technique set forth above, substrates with patterns having regions of different chemical characteristics can be produced. Thus, for example, a pattern having an array of adjacent isolated features is created by varying the hydrophobicity/hydrophilicity, charge and other chemical characteristics of the pattern constituents. For example, hydrophilic compounds can be confined to individual hydrophilic features by patterning "walls" between the adjacent features using hydrophobic materials. Similarly, positively or negatively charged compounds can be confined to features having "walls" made of compounds with charges similar to those of the confined compounds. Similar substrate configurations are accessible through microprinting a layer with the desired characteristics directly onto the substrate. See, Mrkish, M.; Whitesides, G. M., *Ann. Rev. Biophys. Biomol. Struct.* 25:55-78 (1996).

The specificity and multiplexing capacity of the chips of the invention can be increased by incorporating spatial encoding (e.g., spotted microarrays) into the chip substrate. Spatial encoding can be introduced into each of the chips of the invention. In an exemplary embodiment, binding functionalities for different analytes can be arrayed across the chip surface, allowing specific data codes (e.g., target-binding functionality specificity) to be reused in each location. In this case, the array location is an additional encoding parameter, allowing the detection of a virtually unlimited number of different analytes.

While a large number of targets can be detected simultaneously using a spatial array, the time involved to scan all array positions may limit the ease of use for larger arrays.

In the embodiments of the invention in which spatial encoding is utilized, they utilize a spatially encoded array comprising m binding functionalities distributed over m regions of the substrate. Each of the m binding functionalities is preferably a different functionality, although chips in which the same functionality is located in two or more locations are within the scope of the present invention. The m binding functionalities are preferably patterned on the substrate in a manner that allows the identity of each of the m locations to be ascertained. In a preferred embodiment, the m binding functionalities are ordered in a p by q matrix of (p×q) discrete locations, wherein each of the (p×q) locations has bound thereto at least one of the m binding functionalities. The microarray can be patterned from essentially any type of binding functionality.

The spatially encoded assay substrates can include substantially any number of compounds. In a preferred embodiment, m is a number from 1 to 100, more preferably, from 10 to 1,000, and more preferably from 100 to 10,000.

The spatially encoded assay substrates can include essentially any number of compounds. In an embodiment in which the binding functionalities are polynucleotides (oligonucleotides or nucleic acids) or polypeptides, m is a number from 1 to 100, more preferably, from 10 to 1,000, and more preferably from 100 to 10,000.

In a particularly preferred embodiment, the substrate includes an aluminum support that is coated with a layer of silicon dioxide. In yet a further preferred embodiment, the silicon dioxide layer is from about 1000-3000 Å in thickness.

Those of skill in the art will appreciate that the above-described and other methods are useful for preparing arrays of a wide variety of compounds in addition to nucleic acids, are useful for preparing arrays of a wide variety of compounds in addition to nucleic acids.

Adsorbent Layer

In a preferred embodiment, the adsorbent layer of the chips of the invention are configured such that detection of the immobilized analyte does not require elution, recovery, amplification, or labeling of the target analyte. Moreover, in another embodiment, the detection of one or more molecular recognition events, at one or more locations within the addressable adsorbent film, does not require removal or consumption of more than a small fraction of the total adsorbent-analyte complex. Thus, the unused portion can be interrogated further after one or more "secondary processing" events conducted directly in situ (i.e., within the boundary of the addressable location) for the purpose of structure and function elucidation, including further assembly or disassembly, modification, or amplification (directly or indirectly).

Adsorbents with improved specificity for an analyte can be developed by an iterative process, referred to as "progressive resolution," in which adsorbents or eluants proven to retain an analyte are tested with additional variables to identity combinations with better binding characteristics.

The adsorbent film is attached to the linker arm layer by one of many interaction modalities with which one of skill in the art is familiar. Representative modalities include, but are not limited to, covalent attachment, attachment via polymer entanglement and electrostatic attachment. In a preferred embodiment, the layer is immobilized onto the surface by its copolymerization with a reactive group on the anchor moiety that is a locus of attachment for the adsorbent layer onto the surface.

Anchor Moiety

A number of reaction types are available for the functionalization of a substrate surface with an anchor moiety. For example, substrates constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced poly-tetrafluoroethylene. Other methods of derivatizing polymeric substrates are known to those of skill in the art.

In an exemplary embodiment the substrate is made of glass or another base material that is coated with a glass-like material and, thus, presents a surface with reactive Si—OH bonds. When the anchor moiety is attached to glass, the anchor moiety will generally include a first functional group of reactivity complementary to the bonds at the surface of the glass.

A number of siloxane functionalizing reagents can be used to form the anchor moiety. Exemplary reagents include, but are not limited to:
1. hydroxyalkyl siloxanes (Silylate surface, functionalize with diborane, and $H_2O_2$ to oxidize the alcohol)
   a. allyl trichlorosilane→→3-hydroxypropyl,
   b. 7-oct-1-enyl trichlorchlorosilane→→8-hydroxyoctyl;
2. diol (dihydroxyalkyl) siloxanes (silylate surface and hydrolyze to diol)
   a. (glycidyl trimethoxysilane→→(2,3-dihydroxypropyloxy)propyl;
3. aminoalkyl siloxanes (amines requiring no intermediate functionalizing step)
   a. 3-aminopropyl trimethoxysilane→aminopropyl;
4. dimeric secondary aminoalkyl siloxanes
   a. bis(3-trimethoxysilylpropyl) amine→bis(silyloxylpropyl)amine; and unsaturated species (e.g., acryloyl, methacryloyl, styryl, etc.).

In a still further exemplary embodiment, the anchor moiety is derived from a species having a structure according to Formula III:

$$(RO)_3-Si-R^1-X^1 \tag{III}$$

in which R is an alkyl group, such as methyl or ethyl, $R^1$ is a linking group between silicon and $X^1$, and $X^1$ is a reactive group or a protected reactive group. The reactive group can also be a member of the adsorbent layer as discussed below. Silane derivatives having halogens or other leaving groups beside the displayed alkoxy groups are also useful in the present invention.

In a presently preferred embodiment, the anchor moiety is derived from a member selected from styrylethyltrimethoxysilane, styrylethylmethyldimethoxysilane, styrylethyldimethylmethoxysilane, styrylethyltrichlorosilane, styrylethylmethyldimethoxysilane, styrylethyldimethylmethoxysilane, (3-acryloxypropyl)trimethoxysilane, (3-acryloxypropyl)methyldimethoxysilane, (3-acryloxypropyl)dimethylmethoxysilane, (3-acryloxypropyl)trichlorosilane, (3-acryloxypropyl)methyldichlorosilane, (3-acryloxypropyl) dimethylchlorosilane, (3-methacryloxypropyl) trimethoxysilane, (3-methacryloxypropyl) methyldimethoxysilane, (3-methacryloxypropyl) dimethylmethoxysilane, (3-methacryloxypropyl) trichlorosilane, (3-methacryloxypropyl) methyldichlorosilane, (3-methacryloxypropyl) dimethylchlorosilane and combinations thereof.

In another exemplary embodiment, the substrate is at least partially a metal film, such as a gold film, and the reactive group is tethered to the metal surface by an agent displaying avidity for that surface. In a presently preferred embodiment, the substrate is at least partially a gold film and the group, which reacts with the metal surface includes a thiol, sulfide or disulfide according to Formula IV:

$$Y-S-R^2-X^2 \quad (IV)$$

in which $R^2$ is a linking group between sulfur and $X^2$, and $X^2$ is a reactive group or a protected reactive group. $X^2$ can also be a member of the adsorbent film. Y is a member selected from the group consisting of H, $R^3$ and $R^3-S-$, wherein $R^2$ and $R^3$ are independently selected.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding haloamines, halo-carboxylic acids, etc. by reaction of these halo precursors with sodium sulfhydride. See, for example, Reid, Organic Chemistry of Bivalent Sulfur, vol. 1, pp. 21-29, 32-35, vol. 5, pp. 27-34, Chemical Publishing Co., New York, 1958, 1963. Additionally, functionalized sulfides can be prepared via alkylthio-de-halogenation with a mercaptan salt. See, Reid, Organic Chemistry of Bivalent Sulfur, vol. 2, pp. 16-21, 24-29, vol. 3, pp. 11-14, Chemical Publishing Co., New York, 1960. Other methods for producing compounds useful in practicing the present invention will be apparent to those of skill in the art.

In another preferred embodiment, the anchor moiety provides for more than one reactive group per each anchor moiety. Using a reagent such as that shown below in Formula V, each reactive site on the substrate surface, which is bound to an anchor moiety, is "amplified" into two or more reactive groups.

$$(RO)_3-Si-R^1-(X^1)_n \quad (V)$$

In Formula 3, R is an alkyl group, such as methyl, $R^1$ is a linking group between silicon and $X^1$, $X^1$ is a reactive group or a protected reactive group and n is an integer between 2 and 50, and more preferably between 2 and 20.

Similar amplifying molecules are also of use in those embodiments wherein the substrate is at least partially a metal film. In these embodiments the group, which reacts with the metal surface comprises a thiol, sulfide or disulfide such as in Formula VI:

$$Y-S-R^2-(X^2)_n \quad (VI)$$

in which the symbols $R^2$, $X^2$, Y, $R^3$ have substantially the same meanings discussed above.

Exemplary R groups of use for $R^1$, $R^2$ and $R^3$ in the above described embodiments of the present invention include, but are not limited to, substituted or unsubstituted alkyl, substituted or unsubstituted heteroalkyl, substituted or unsubstituted aryl, acyl, alkylamino, acylamino, alkoxy, acyloxy, aryloxy, aryloxyalkyl, substituted or unsubstituted heteroaryl, substituted or unsubstituted heterocyclyl.

In each of Formulae II-VI, above, each of $R^1$, $R^2$ and $R^3$ are either stable or they can be cleaved by chemical or photochemical reactions. For example, an anchor moiety that includes an ester or disulfide bond can be cleaved by hydrolysis and reduction, respectively. Upon cleavage, the adsorbent film is released from the substrate. Also within the scope of the present invention is the use of groups, which are cleaved by light such as, for example, nitrobenzyl derivatives, phenacyl groups, benzoin esters, etc. Other such cleaveable groups are well known to those of skill in the art. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989).

Reactive Functional Groups

The reactive functional group serves as a locus of attachment for tethering the adsorbent layer to the anchor moiety. In a presently preferred embodiment, the reactive functional group is complementary to a reactive group on a component of the adsorbent layer. In an exemplary embodiment utilizing a complementary functional group, one or more monomer or cross-linking group is covalently bound to the anchor moiety via the reactive functional group. A polymerization reaction is then carried out, producing a hydrogel that is linked to the substrate. In a further preferred embodiment, the reactive group is capable of participating in a polymerization reaction with one or more component of the absorbent layer.

Exemplary reactive functional groups ($X^1$ and $X^2$) include:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, radical polymerization, acylation, Michael addition, etc; and (j) epoxides which can react with, for example, amines and hydroxyl compounds.

The reactive functional groups can be chosen such that they do not participate in, or interfere with, the reaction controlling the attachment of the anchor moiety to the substrate. Alternatively, the reactive functional group can be protected from participating in the reaction by the presence of a protecting group. Those of skill in the art will understand how to protect a particular functional group from interfering with a chosen set of reaction conditions. For examples of useful protecting groups, See Greene et al., Protective Groups in Organic Synthesis, John Wiley & Sons, New York, 1991.

Analytes

The methods of the present invention can be used to detect any target, or class of targets, which interact with a binding functionality in a detectable manner. The interaction between the target and binding functionality can be any physicochemical interaction, including covalent bonding, ionic bonding, hydrogen bonding, van der Waals interactions, attractive electronic interactions and hydrophobic/hydrophilic interactions.

In an exemplary embodiment, the interaction is an ionic interaction. In this embodiment, an acid, base, metal ion or metal ion-binding ligand is the target. In a further exemplary embodiment, the interaction is a hydrogen bonding interaction.

In a preferred embodiment, the target molecule is a biomolecule such as a polypeptide (e.g., peptide or protein), a polynucleotide (e.g., oligonucleotide or nucleic acid), a carbohydrate (e.g., simple or complex carbohydrate) or a lipid (e.g., fatty acid or polyglycerides, phospholipids, etc.). In the case of proteins, the nature of the target can depend upon the nature of the binding functionality. For example, one can capture a ligand using a receptor for the ligand as a binding functionality; an antigen using an antibody against the antigen, or a substrate using an enzyme that acts on the substrate.

The target can be derived from any sort of biological source, including body fluids such as blood, serum, saliva, urine, seminal fluid, seminal plasma, lymph, and the like. It also includes extracts from biological samples, such as cell lysates, cell culture media, or the like. For example, cell lysate samples are optionally derived from, e.g., primary tissue or cells, cultured tissue or cells, normal tissue or cells, diseased tissue or cells, benign tissue or cells, cancerous tissue or cells, salivary glandular tissue or cells, intestinal tissue or cells, neural tissue or cells, renal tissue or cells, lymphatic tissue or cells, bladder tissue or cells, prostatic tissue or cells, urogenital tissues or cells, tumoral tissue or cells, tumoral neovasculature tissue or cells, or the like.

In another embodiment, the target is a member selected from the group consisting of acids, bases, organic ions, inorganic ions, pharmaceuticals, herbicides, pesticides, and noxious gases. Each of these targets can be detected as a vapor or a liquid. The target can be present as a component in a mixture of structurally unrelated compounds, an assay mixture, racemic mixtures of stereoisomers, non-racemic mixtures of stereoisomers, mixtures of diastereomers, mixtures of positional isomers or as a pure compound. Within the scope of the invention is method to detect a particular target of interest without interference from other substances within a mixture.

The target can be labeled with a fluorophore or other detectable group either directly or indirectly through interacting with a second species to which a detectable group is bound. When a second labeled species is used as an indirect labeling agent, it is selected from any species that is known to interact with the target species. Preferred second labeled species include, but are not limited to, antibodies, aptazymes, aptamers, streptavidin, and biotin.

The target can be labeled either before or after it interacts with the binding functionality. The target molecule can be labeled with a detectable group or more than one detectable group. Where the target species is multiply labeled with more than one detectable group, the groups are preferably distinguishable from each other. Properties on the basis of which the individual quantum dots can be distinguished include, but are not limited to, fluorescence wavelength, absorption wavelength, fluorescence emission, fluorescence absorption, ultraviolet light absorbance, visible light absorbance, fluorescence quantum yield, fluorescence lifetime, light scattering and combinations thereof.

G. Assays

The chip of the present invention is useful in performing assays of substantially any format including, but not limited to chromatographic capture, immunoassays, competitive assays, DNA or RNA binding assays, fluorescence in situ hybridization (FISH), protein and nucleic acid profiling assays, sandwich assays and the like. The following discussion focuses on the use of the methods of the invention in practicing exemplary assays. This focus is for clarity of illustration only and is not intended to define or limit the scope of the invention. Those of skill in the art will appreciate that the method of the invention is broadly applicable to any assay technique for detecting the presence and/or amount of a target.

The chip of the present invention is useful for performing retentate chromatography. Retentate chromatography has many uses in biology and medicine. These uses include combinatorial biochemical separation and purification of analytes, protein profiling of biological samples, the study of differential protein expression and molecular recognition events, diagnostics and drug discovery. Retentate chromatography is described in Hutchens and Yip, U.S. Pat. No. 6,225,047.

One basic use of retentate chromatography as an analytical tool involves exposing a sample to a combinatorial assortment of different adsorbent/eluant combinations and detecting the behavior of the analyte under the different conditions. This both purifies the analyte and identifies conditions useful for detecting the analyte in a sample. Substrates having adsorbents identified in this way can be used as specific detectors of the analyte or analytes. In a progressive extraction method, a sample is exposed to a first adsorbent/eluant combination and the wash, depleted of analytes that are adsorbed by the first adsorbent, is exposed to a second adsorbent to deplete it of other analytes. Selectivity conditions identified to retain analytes also can be used in preparative purification procedures in which an impure sample containing an analyte is exposed, sequentially, to adsorbents that retain it, impurities are removed, and the retained analyte is collected from the adsorbent for a subsequent round. See, for example, U.S. Pat. No. 6,225,047.

The chip of the invention is useful in applications such as sequential extraction of analytes from a solution, progressive resolution of analytes in a sample, preparative purification of an analyte, making probes for specific detection of analytes, methods for identifying proteins, methods for assembling multimeric molecules, methods for performing enzyme assays, methods for identifying analytes that are differentially expressed between biological sources, methods for identifying ligands for a receptor, methods for drug discovery (e.g., screening assays), and methods for generating agents that specifically bind an analyte.

In other applications, chip-based assays based on specific binding reactions are useful to detect a wide variety of targets such as drugs, hormones, enzymes, proteins, antibodies, and infectious agents in various biological fluids and tissue samples. In general, the assays consist of a target, a binding functionality for the target, and a means of detecting the target after its immobilization by the binding functionality (e.g., a detectable label). Immunological assays involve reactions between immunoglobulins (antibodies), which are capable of binding with specific antigenic determinants of various compounds and materials (antigens). Other types of reactions include binding between avidin and biotin, protein A and immunoglobulins, lectins and sugar moieties and the like. See, for example, U.S. Pat. No. 4,313,734, issued to Leuvering; U.S. Pat. No. 4,435,504, issued to Zuk; U.S. Pat. Nos. 4,452,901 and 4,960,691, issued to Gordon; and U.S. Pat. No. 3,893,808, issued to Campbell.

The present invention provides a chip useful for performing assays that are useful for confirming the presence or absence of a target in a sample and for quantitating a target in a sample. An exemplary assay format with which the invention can be used is an immunoassay, e.g., competitive assays, and sandwich assays. The invention is further illustrated using these two assay formats. The focus of the following discussion on competitive assays and sandwich assays is for clarity of illustration and is not intended to either define or limit the scope of the invention. Those of skill in the art will appreciate that the invention described herein can be practiced in conjunction with a number of other assay formats.

In an exemplary competitive binding assay, two species, one of which is the target, compete for a binding functionality on an adsorbent film. After an incubation period, unbound materials are washed off and the amount of target, or other species bound to the functionality is compared to reference amounts for determination of the target, or other species concentration in the assay mixture. Other competitive assay motifs using labeled target and/or labeled binding functionality and/or labeled reagents will be apparent to those of skill in the art.

A second type of assay is known as a sandwich assay and generally involves contacting an assay mixture with a surface having immobilized thereon a first binding functionality immunologically specific for that target. A second solution comprising a detectable binding material is then added to the assay. The labeled binding material will bind to a target, which is bound to the binding functionality. The assay system is then subjected to a wash step to remove labeled binding material, which failed to bind with the target and the amount of detectable material remaining on the chip is ordinarily proportional to the amount of bound target. In representative assays one or more of the target, binding functionality or binding material is labeled with a fluorescent label.

In addition to detecting an interaction between a binding functionality and a target, it is frequently desired to quantitate the magnitude of the affinity between two or more binding partners. The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

The binding of an antagonist to a receptor can be assayed by a competitive binding method using a ligand for that receptor and the antagonist. One of the three binding partners (i.e., the ligand, antagonist or receptor) is bound to the binding functionality, or is the binding functionality. In an exemplary embodiment, the receptor is bound to the adsorbent film. Various concentrations of ligand are added to different chip regions. A detectable antagonist is then applied to each region to a chosen final concentration. The treated chip will generally be incubated at room temperature for a preselected time. The receptor-bound antagonist can be separated from the unbound antagonist by filtration, washing or a combination of these techniques. Bound antagonist remaining on the chip can be measured as discussed herein. A number of variations on this general experimental procedure will be apparent to those of skill in the art.

Competition binding data can be analyzed by a number of techniques, including nonlinear least-squares curve fitting procedure. When the ligand is an antagonist for the receptor, this method provides the IC50 of the antagonist (concentration of the antagonist which inhibits specific binding of the ligand by 50% at equilibrium). The IC50 is related to the equilibrium dissociation constant (Ki) of the antagonist based on the Cheng and Prusoff equation: $Ki=IC50/(1+L/Kd)$, where L is the concentration of the ligand used in the competitive binding assay, and Kd is the dissociation constant of the ligand as determined by Scatchard analysis. These assays are described, among other places, in Maddox et al., *J Exp Med.*, 158: 1211 (1983); Hampton et al., Serological Methods, A Laboratory Manual, APS Press, St. Paul, Minn., 1990.

The chip and method of the present invention are also of use in screening libraries of compounds, such as combinatorial libraries. The synthesis and screening of chemical libraries to identify compounds, which have novel bioactivities, and material science properties is now a common practice. Libraries that have been synthesized include, for example, collections of oligonucleotides, oligopeptides, and small and large molecular weight organic or inorganic molecules. See, Moran et al., PCT Publication WO 97/35198, published Sep. 25, 1997; Baindur et al., PCT Publication WO 96/40732, published Dec. 19, 1996; Gallop et al., *J. Med. Chem.* 37:1233-51 (1994).

Virtually any type of compound library can be probed using the method of the invention, including peptides, nucleic acids, saccharides, small and large molecular weight organic and inorganic compounds. In a presently preferred embodiment, the libraries synthesized comprise more than 10 unique compounds, preferably more than 100 unique compounds and more preferably more than 1000 unique compounds.

The nature of these libraries is better understood by reference to peptide-based combinatorial libraries as an example. The present invention is useful for assembling peptide-based combinatorial libraries, but it is not limited to these libraries. The methods of the invention can be used to screen libraries of essentially any molecular format, including small organic molecules, carbohydrates, nucleic acids, polymers, organometallic compounds and the like. Thus, the following discussion, while focusing on peptide libraries, is intended to be illustrative and not limiting.

Libraries of peptides and certain types of peptide mimetics, called "peptoids", are assembled and screened for a desirable biological activity by a range of methodologies (see, Gordon et al., *J. Med Chem.*, 37: 1385-1401 (1994); Geysen, (*Bioorg. Med. Chem. Letters,* 3: 397-404 (1993); *Proc. Natl. Acad Sci. USA,* 81: 3998 (1984); Houghton, *Proc. Natl. Acad. Sci. USA,* 82: 5131 (1985); Eichler et al., *Biochemistry,* 32: 11035-11041 (1993); and U.S. Pat. No. 4,631,211); Fodor et al., *Science,* 251: 767 (1991); Huebner et al. (U.S. Pat. No. 5,182, 366). Small organic molecules have also been prepared by combinatorial means. See, for example, Camps. et al., *Annaks de Quimica,* 70: 848 (1990); U.S. Pat. No. 5,288,514; U.S. Pat. No. 5,324,483; Chen et al., *J. Am. Chem. Soc.,* 116: 2661-2662 (1994).

In an exemplary embodiment, a binding domain of a receptor, for example, serves as the focal point for a drug discovery assay, where, for example, the receptor is immobilized, and incubated both with agents (i.e., ligands) known to interact with the binding domain thereof, and a quantity of a particular drug or inhibitory agent under test. The extent to which the drug binds with the receptor and thereby inhibits receptor-ligand complex formation can then be measured. Such possibilities for drug discovery assays are contemplated herein and are considered within the scope of the present invention. Other focal points and appropriate assay formats will be apparent to those of skill in the art.

Detection

The presence of the analyte immobilized on the adsorbent film and changes in the adsorbent film upon binding of the analyte can be detected by the use of microscopes, spectrometry, electrical techniques and the like. For example, in certain embodiments light in the visible region of the spectrum is used to illuminate details of the adsorbent film (e.g., reflectance, transmittance, birefringence, diffraction, etc.). Alternatively, the light can be passed through the adsorbent film and the amount of light transmitted, absorbed or reflected can be measured. The device can utilize a backlighting device such as that described in U.S. Pat. No. 5,739,879. Light in the ultraviolet and infrared regions is also of use in the present invention.

For the detection of low concentrations of analytes in the field of diagnostics, the methods of chemiluminescence and electrochemiluminescence are gaining wide-spread use. These methods of chemiluminescence and electro-chemiluminescence provide a means to detect low concentrations of analytes by amplifying the number of luminescent molecules or photon generating events many-fold, the resulting "signal amplification" then allowing for detection of low concentration analytes.

In another embodiment, a fluorescent label is used to label one or more assay component or region of the chip. Fluorescent labels have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Many fluorescent labels are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful in the present invention. Such proteins include, for example, green fluorescent proteins of cnidarians (Ward et al., *Photochem. Photobiol.* 35:803-808 (1982); Levine et al., *Comp. Biochem. Physiol.,* 72B:77-85 (1982)), yellow fluorescent protein from *Vibrio fischeri* strain (Baldwin et al., *Biochemistry* 29:5509-15 (1990)), Peridinin-chlorophyll from the dinoflagellate Symbiodinium sp. (Morris et al., *Plant Molecular Biology* 24:673:77 (1994)), phycobiliproteins from marine cyanobacteria, such as Synechococcus, e.g., phycoerythrin and phycocyanin (Wilbanks et al., *J. Biol. Chem.* 268:1226-35 (1993)), and the like.

Microscopic techniques of use in practicing the invention include, but are not limited to, simple light microscopy, confocal microscopy, polarized light microscopy, atomic force microscopy (Hu et al., *Langmuir* 13:5114-5119 (1997)), scanning tunneling microscopy (Evoy et al., *J. Vac. Sci. Technol A* 15:1438-1441, Part 2 (1997)), and the like.

Spectroscopic techniques of use in practicing the present invention include, for example, infrared spectroscopy (Zhao et al., *Langmuir* 13:2359-2362 (1997)), raman spectroscopy (Zhu et al., *Chem. Phys. Lett.* 265:334-340 (1997)), X-ray photoelectron spectroscopy (Jiang et al., *Bioelectroch. Bioener.* 42:15-23 (1997)) and the like. Visible and ultraviolet spectroscopies are also of use in the present invention.

Other useful techniques include, for example, surface plasmon resonance (Evans et al., *J. Phys. Chem. B* 101:2143-2148 (1997), ellipsometry (Harke et al., *Thin Solid Films* 285:412-416 (1996)), impedometric methods (Rickert et al., *Biosens. Bioelectron.* 11:757:768 (1996)), and the like.

In addition, the Polymerase Chain Reaction (PCR) and other related techniques have gained wide use for amplifying the number of nucleic acid analytes in a sample. By the addition of appropriate enzymes, reagents, and temperature cycling methods, the number of nucleic acid analyte molecules are amplified such that the analyte can be detected by most known detection means.

Of particular interest is the use of mass spectrometric techniques to detect analytes immobilized on the adsorbent film, particularly those mass spectrometric methods utilizing desorption of the analyte from the adsorbent and direct detection of the desorbed analytes. Analytes retained by the adsorbent after washing are adsorbed to the substrate. Analytes retained on the substrate are detected by desorption spectrometry.

Desorbing the analyte from the adsorbent involves exposing the analyte to an appropriate energy source. Usually this means striking the analyte with radiant energy or energetic particles. For example, the energy can be light energy in the form of laser energy (e.g., UV laser) or energy from a flash lamp. Alternatively, the energy can be a stream of fast atoms. Heat may also be used to induce/aid desorption.

The biochips of this invention are useful for surface-enhanced laser desorption/ionization, or SELDI. SELDI represents a significant advance over MALDI in terms of specificity, selectivity and sensitivity. In MALDI, the analyte solution is mixed with a matrix solution and the mixture is allowed to crystallize after being deposited on an inert probe surface, trapping the analyte. The matrix is selected to absorb the laser energy and apparently impart it to the analyte, resulting in desorption and ionization. Generally, the matrix absorbs in the UV range. MALDI for large proteins is described in, e.g., U.S. Pat. No. 5,118,937 (Hillenkamp et al.) and U.S. Pat. No. 5,045,694 (Beavis and Chait).

SELDI is described in U.S. Pat. No. 5,719,060 (Hutchens and Yip). SELDI is a method for desorption in which the analyte is presented to the energy stream on a surface that captures the analyte and, thereby, enhances analyte capture and/or desorption.

One version of SELDI, called SEAC (Surface-Enhanced Affinity Capture), involves presenting the analyte to the desorbing energy in association with an affinity capture device (i.e., an adsorbent) attached to probe surface. When an analyte is so adsorbed, the desorbing energy source is provided with a greater opportunity to desorb the target analyte. An energy absorbing material, e.g., matrix, usually is added to the probe to aid desorption of biomolecules, prior to presenting the probe to the energy source, e.g., laser, for desorbing the analyte. Typically used matrix materials include sinapinic acid (SPA) and alpha-cyano-4-hydroxy cinnamic acid (CHCA).

The desorbed analyte can be detected by any of several means. When the analyte is ionized in the process of desorption, such as in laser desorption/ionization mass spectrometry, the detector can be an ion detector. Mass spectrometers generally include means for determining the time-of-flight of desorbed ions. This information is converted to mass. One need not determine the mass of desorbed ions, however, to resolve and detect them: the fact that ionized analytes strike the detector at different times provides detection and resolution of them.

A plurality of detection means can be implemented in series to fully interrogate the analyte components and function associated with retentate at each location in the array.

Desorption detectors comprise means for desorbing the analyte from the adsorbent and means for directly detecting the desorbed analyte. That is, the desorption detector detects desorbed analyte without an intermediate step of capturing the analyte in another solid phase and subjecting it to subsequent analysis. Detection of an analyte normally will involve detection of signal strength. This, in turn, reflects the quantity of analyte adsorbed to the adsorbent.

The desorption detector also can include other elements, e.g., a means to accelerate the desorbed analyte toward the detector, and a means for determining the time-of-flight of the analyte from desorption to detection by the detector.

A preferred desorption detector is a laser desorption/ionization mass spectrometer, which is well known in the art. The mass spectrometer includes a port into which the substrate that carries the adsorbed analytes, e.g., a probe, is inserted. Striking the analyte with energy, such as laser energy desorbs the analyte. Striking the analyte with the laser results in desorption of the intact analyte into the flight tube and its ionization. The flight tube generally defines a vacuum space. Electrified plates in a portion of the vacuum tube create an electrical potential which accelerate the ionized analyte toward the detector. A clock measures the time of flight and the system electronics determines velocity of the analyte and converts this to mass. As any person skilled in the art understands, any of these elements can be combined with other elements described herein in the assembly of desorption detectors that employ various means of desorption, acceleration, detection, measurement of time, etc. An exemplary detector further includes a means for translating the surface so that any spot on the array is brought into line with the laser beam.

Informatics

As high-resolution, high-sensitivity datasets acquired using the methods of the invention become available to the art, significant progress in the areas of diagnostics, therapeutics, drug development, biosensor development, and other related areas will occur. For example, disease markers can be identified and utilized for better confirmation of a disease condition or stage (see, U.S. Pat. Nos. 5,672,480; 5,599,677; 5,939,533; and 5,710,007). Subcellular toxicological information can be generated to better direct drug structure and activity correlation (see, Anderson, L., "Pharmaceutical Proteomics: Targets, Mechanism, and Function," paper presented at the IBC Proteomics conference, Coronado, Calif. (Jun. 11-12, 1998)). Subcellular toxicological information can also be utilized in a biological sensor device to predict the likely toxicological effect of chemical exposures and likely tolerable exposure thresholds (see, U.S. Pat. No. 5,811,231). Similar advantages accrue from datasets relevant to other biomolecules and bioactive agents (e.g., nucleic acids, saccharides, lipids, drugs, and the like).

Thus, in another preferred embodiment, the present invention provides a database that includes at least one set of data assay data. The data contained in the database is acquired using a method of the invention and/or a QD-labeled species of the invention either singly or in a library format. The database can be in substantially any form in which data can be maintained and transmitted, but is preferably an electronic database. The electronic database of the invention can be maintained on any electronic device allowing for the storage of and access to the database, such as a personal computer, but is preferably distributed on a wide area network, such as the World Wide Web.

The focus of the present section on databases, which include peptide sequence specificity data is for clarity of illustration only. It will be apparent to those of skill in the art that similar databases can be assembled for any assay data acquired using an assay of the invention.

The compositions and methods described herein for identifying and/or quantitating the relative and/or absolute abundance of a variety of molecular and macromolecular species from a biological sample provide an abundance of information, which can be correlated with pathological conditions, predisposition to disease, drug testing, therapeutic monitoring, gene-disease causal linkages, identification of correlates of immunity and physiological status, among others. Although the data generated from the assays of the invention is suited for manual review and analysis, in a preferred embodiment, prior data processing using high-speed computers is utilized.

An array of methods for indexing and retrieving biomolecular information is known in the art. For example, U.S. Pat. Nos. 6,023,659 and 5,966,712 disclose a relational database system for storing biomolecular sequence information in a manner that allows sequences to be catalogued and searched according to one or more protein function hierarchies. U.S. Pat. No. 5,953,727 discloses a relational database having sequence records containing information in a format that allows a collection of partial-length DNA sequences to be catalogued and searched according to association with one or more sequencing projects for obtaining full-length sequences from the collection of partial length sequences. U.S. Pat. No. 5,706,498 discloses a gene database retrieval system for making a retrieval of a gene sequence similar to a sequence data item in a gene database based on the degree of similarity between a key sequence and a target sequence. U.S. Pat. No. 5,538,897 discloses a method using mass spectroscopy fragmentation patterns of peptides to identify amino acid sequences in computer databases by comparison of predicted mass spectra with experimentally-derived mass spectra using a closeness-of-fit measure. U.S. Pat. No. 5,926,818 discloses a multi-dimensional database comprising a functionality for multi-dimensional data analysis described as on-line analytical processing (OLAP), which entails the consolidation of projected and actual data according to more than one consolidation path or dimension. U.S. Pat. No. 5,295,261 reports a hybrid database structure in which the fields of each database record are divided into two classes, navigational and informational data, with navigational fields stored in a hierarchical topological map which can be viewed as a tree structure or as the merger of two or more such tree structures.

The present invention provides a computer database comprising a computer and software for storing in computer-retrievable form assay data records cross-tabulated, for example, with data specifying the source of the target-containing sample from which each sequence specificity record was obtained.

In an exemplary embodiment, at least one of the sources of target-containing sample is from a tissue sample known to be free of pathological disorders. In a variation, at least one of the sources is a known pathological tissue specimen, for example, a neoplastic lesion or a tissue specimen containing a pathogen such as a virus, bacteria or the like. In another variation, the assay records cross-tabulate one or more of the following parameters for each target species in a sample: (1) a unique identification code, which can include, for example, a target molecular structure and/or characteristic separation coordinate (e.g., electrophoretic coordinates); (2) sample source; and (3) absolute and/or relative quantity of the target species present in the sample.

The invention also provides for the storage and retrieval of a collection of target data in a computer data storage apparatus, which can include magnetic disks, optical disks, magneto-optical disks, DRAM, SRAM, SGRAM, SDRAM, RDRAM, DDR RAM, magnetic bubble memory devices, and other data storage devices, including CPU registers and on-CPU data storage arrays. Typically, the target data records are stored as a bit pattern in an array of magnetic domains on a magnetizable medium or as an array of charge states or transistor gate states, such as an array of cells in a DRAM device (e.g., each cell comprised of a transistor and a charge storage area, which may be on the transistor). In one embodiment, the invention provides such storage devices, and computer systems built therewith, comprising a bit pattern encoding a protein expression fingerprint record comprising unique identifiers for at least 10 target data records cross-tabulated with target source.

When the target is a peptide or nucleic acid, the invention preferably provides a method for identifying related peptide or nucleic acid sequences, comprising performing a computerized comparison between a peptide or nucleic acid sequence assay record stored in or retrieved from a computer storage device or database and at least one other sequence. The comparison can include a sequence analysis or comparison algorithm or computer program embodiment thereof (e.g., FASTA, TFASTA, GAP, BESTFIT) and/or the comparison may be of the relative amount of a peptide or nucleic acid sequence in a pool of sequences determined from a polypeptide or nucleic acid sample of a specimen.

The invention also preferably provides a magnetic disk, such as an IBM-compatible (DOS operating system, WINDOWS® operating system, WINDOWS95/98/2000® operating systems, WINDOWS® NT(R) operating system, OS/2® operating system) or other format (e.g. LINUX® operating system, SUNOS™ operating system, SOLARIS™ operating system, AIX operating system, SCO UNIX® operating system, VMS operating system, MV operating system, MACINTOSH® operating system, etc.) floppy diskette or hard (fixed, Winchester) disk drive, comprising a bit pattern encoding data from an assay of the invention in a file format suitable for retrieval and processing in a computerized sequence, analysis, comparison, or relative quantitation method.

The invention also provides a network, comprising a plurality of computing devices linked via a data link, such as an Ethernet cable (coax or 10BaseT), telephone line, ISDN line, wireless network, optical fiber, or other suitable signal tranmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The invention also provides a method for transmitting assay data that includes generating an electronic signal on an electronic communications device, such as a modem, ISDN terminal adapter, DSL, cable modem, ATM switch, or the like, wherein the signal includes (in native or encrypted format) a bit pattern encoding data from an assay or a database comprising a plurality of assay results obtained by the method of the invention.

In a preferred embodiment, the invention provides a computer system for comparing a query target to a database containing an array of data structures, such as an assay result obtained by the method of the invention, and ranking database targets based on the degree of identity and gap weight to the target data. A central processor is preferably initialized to load and execute the computer program for alignment and/or comparison of the assay results. Data for a query target is entered into the central processor via an I/O device. Execution of the computer program results in the central processor retrieving the assay data from the data file, which comprises a binary description of an assay result.

The target data or record and the computer program can be transferred to secondary memory, which is typically random access memory (e.g. DRAM, SRAM, SGRAM, SDRAM). Targets are ranked according to the degree of correspondence between a selected assay characteristic (e.g., binding to selected binding functionality) and the same characteristic of the query target and results are output via an I/O device. For example, a central processor can be a conventional computer (e.g., INTEL® PENTIUM® computer, POWERPC® computer, ALPHA computer, PA-8000 computer, SPARC computer, MIPS 4400 computer, MIPS 10000 computer, VAX computer, etc.); a program can be a commerical or public domain molecular biology software package(e.g., UWGCG Sequence Analysis Software, Darwin); a data file can be optical or magnetic disk, a data server, a memory device, (e.g. DRAM, SRAM, SGRAM, SDRAM, EPROM, bubble memory, flash memory etc.); an I/O device can be a terminal comprising a video display and a keyboard, a modem, an ISDN terminal adapter, an Ethernet port, a punched card reader, a magnetic strip reader, or other suitable I/O device.)

The invention also preferably provides the use of a computer system, such as that described above, which comprises: (1) a computer; (2) a stored bit pattern encoding a collection of peptide sequence specificity records obtained by the methods of the invention, which may be stored in the computer; (3) a comparison target, such as a query target; and (4) a program for alignment and comparison, typically with rank-ordering of comparison results on the basis of computed similarity values.

The materials, methods and devices of the present invention are further illustrated by the examples, which follow. These examples are offered to illustrate, but not to limit the claimed invention.

H. Kits

In a further aspect, the invention provides a kit that allows for the fabrication of a chip of the invention. The kit typically includes one or more component of the adsorbent chip and instructions for preparing the chip. In general, the kit includes one or more monomer and one or more cross-linking agent that can be combined to form a hydrogel of use in the present invention. The kit may also include a, substrate of the chip to which the hydrogel is attached. The kit will also generally provide instructions or access to instructions, e.g. a World Wide Web page link, for preparing a chip of the invention from the components contained in the kit.

In an exemplary embodiment, the invention provides a kit that includes a substrate, and a first container that is charged with a monomeric precursor of a hydrogel ("a monomer"). The monomer is preferably of use in preparing a water swellable hydrogel which binds an analyte through a salt-indpendent hydrophobic attraction; such hydrogels are exemplified herein. The monomer generally includes a hydrophilic moiety and/or a hydrophobic moiety. The kit also includes a second container that is charged with a cross-linking agent that is capable of reacting with the monomer to form a water-swellable hydrogel. The kit additionally includes instructions for combining the monomer and the cross-linking agent to produce a water-swellable hydrogel of use in the invention, and for and for attaching the hydrogel to the surface of the substrate.

Other exemplary kits of the invention include containers charged with monomers and/or cross-linking agents having structures that are different from those in the first and second containers.

The kits of the invention are appropriate for preparing chips on which an analyte is detected via mass spectrometry or another detection method. Both mass spectrometry and other exemplary modes of detection are discussed in greater detail herein.

EXAMPLES

The following examples are offered to illustrate selected embodiments of the present invention and do not limit the scope of the invention.

EXAMPLE 1

1.1 Materials and Methods

Ethanol acetic acid, 2-hydroxy-4-hydroxyethoxyphenyl-2-methylpropanol, sinnapinic acid, trifluoroacetic acid, and acetonitrile were purchased from Aldrich. methoxypropyl trimethoxysilane was purchased from Gelest. Poly(ethylene glycol)dimethacrylate was purchased from Polysciences. Nonylphenoxy-poly(ethylene glycol)methacrylate was purcahsed from Monomer-Polymer & Dajac Lab.

1.2 Silicon Dioxide Coating of Substrate

A flat aluminum (6463-T6) substrate blank having dimensions 9 mm×78 mm was surface derivatized with silicon dioxide by sputtering. Addressable locations ("spots") were created on the substrate surface by coating with a perfluorinated polymer, leaving "holes" in the coating to define the spots.

1.3 Silanation of the Substrate

The silicon dioxide coated substrate was placed into a poly(propylene) box on an orbital shaker. Ethanol (93 mL), deionized water (5 mL) and methacryloxypropyl-trimethoxysilane (2 mL) was added. After agitating the mixture for 2 min, 1N acetic acid (50 µL) was added. The substrate was removed from the reaction mixture and the surface was washed with ethanol and heated to 80° C. for 30 minutes.

In another experiment, the silicon dioxide-coated substrate was placed in an oven and coated with methacryloxypropyl-trimethoxysilane by chemical vapor deposition.

1.4 Copolymerization on the Substrate Surface to Produce H50

2-hydroxy-(4-hydroxyethoxyphenyl)-2-methyl propanone (50 mg), nonylphenoxy-poly(ethylene glycol)methacrylate (1.9 g), and poly(ethylene glycol)dimethacrylate (PEG~1000) (0.1 g) were dissolved in deionized water (10 mL). The above solution is diluted 10-fold by adding ethanol (90 mL). The resulting solution is deposited onto the silanated substrate from Example 1.2 (1.5 µL per spot) and irradiated for 10 min with a near UV exposure system. Following the irradiation, the surface is washed twice with deionized water and once with acetone.

In another experiment, the monomer solution was diluted with 4 g glycerol and 66 g ethanol.

EXAMPLE 2

A binding buffer (5 µL of 1% TFA in water) was loaded in each spot of the chip produced in Example 1. The chip and buffer were incubated at room temperature for 5 minutes, after which the excess buffer was removed from the spots. Sample dissolved in binding buffer (2-3 µL) was loaded into each spot. The chip and sample were incubated for 30 minutes, after which each spot was washed twice with buffer (5 µL), followed by a water wash. To each spot was added saturated EAM (1 µL sinnapinic acid), and the sample was analyzed by mass spectrometry. The results of the analysis are displayed in FIG. 1.

EXAMPLE 3

Example 3 demonstrates the selectivity of H50 for particular analytes using different acetonitrile concentrations in the washing buffer.

The same protocol is used as Example 2 except using 10%, 20% 30%, and 40% acetonitrile in 1% aqueous TFA as washing buffer.

Figure 2:
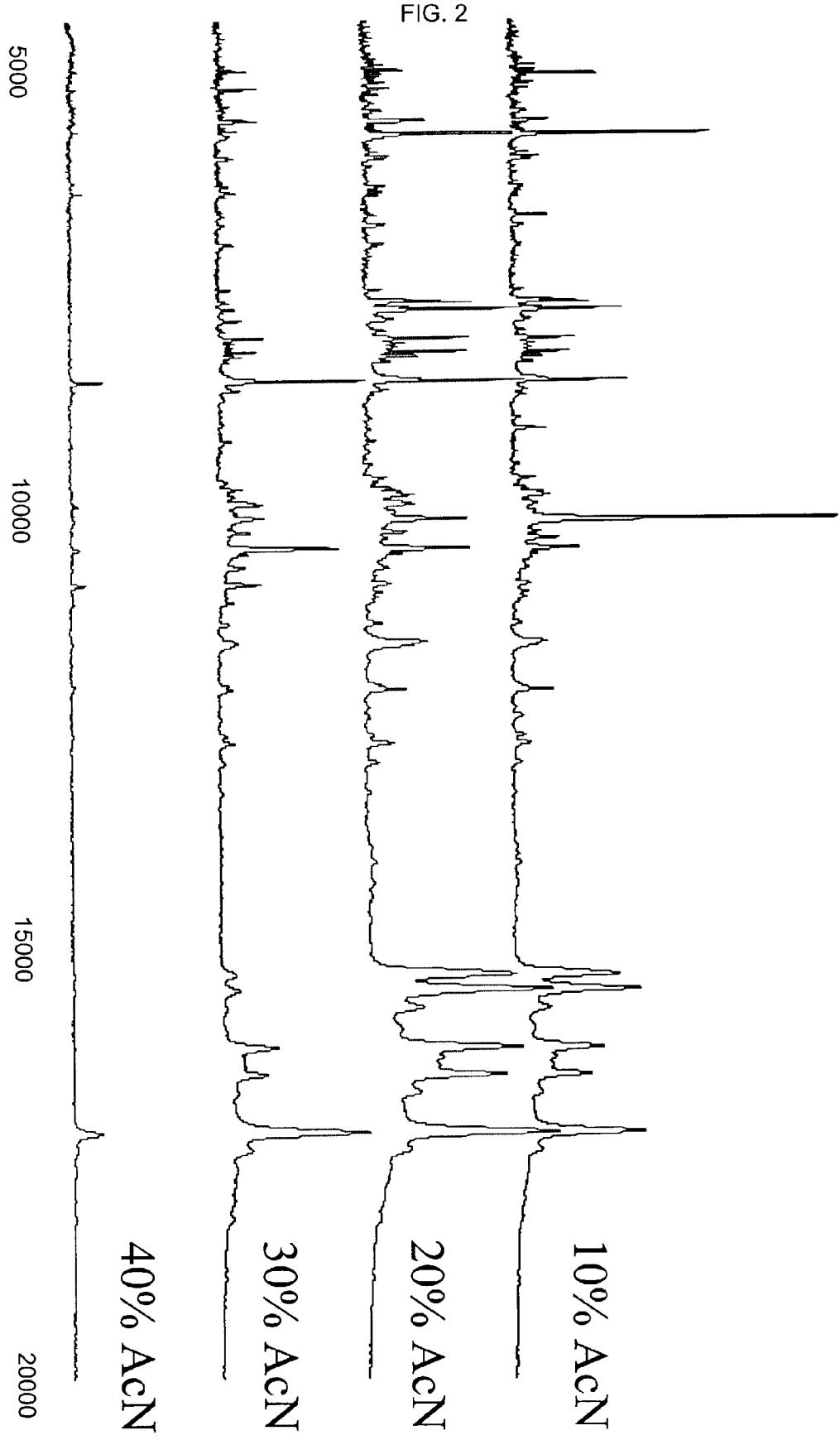
FIG. 2 is a comparison of mass spectra of an extract of rat brain cytosol adsorbed onto a chip of the invention, washed with different concentrations of acetonitrile: (A) 10% acetonitrile; (B) 20% acetonitrile; (C) 30% acetonitrile; and (D) 40% acetonitrile.

Rat Brain Sample: FIG. 2.

Figure 3:
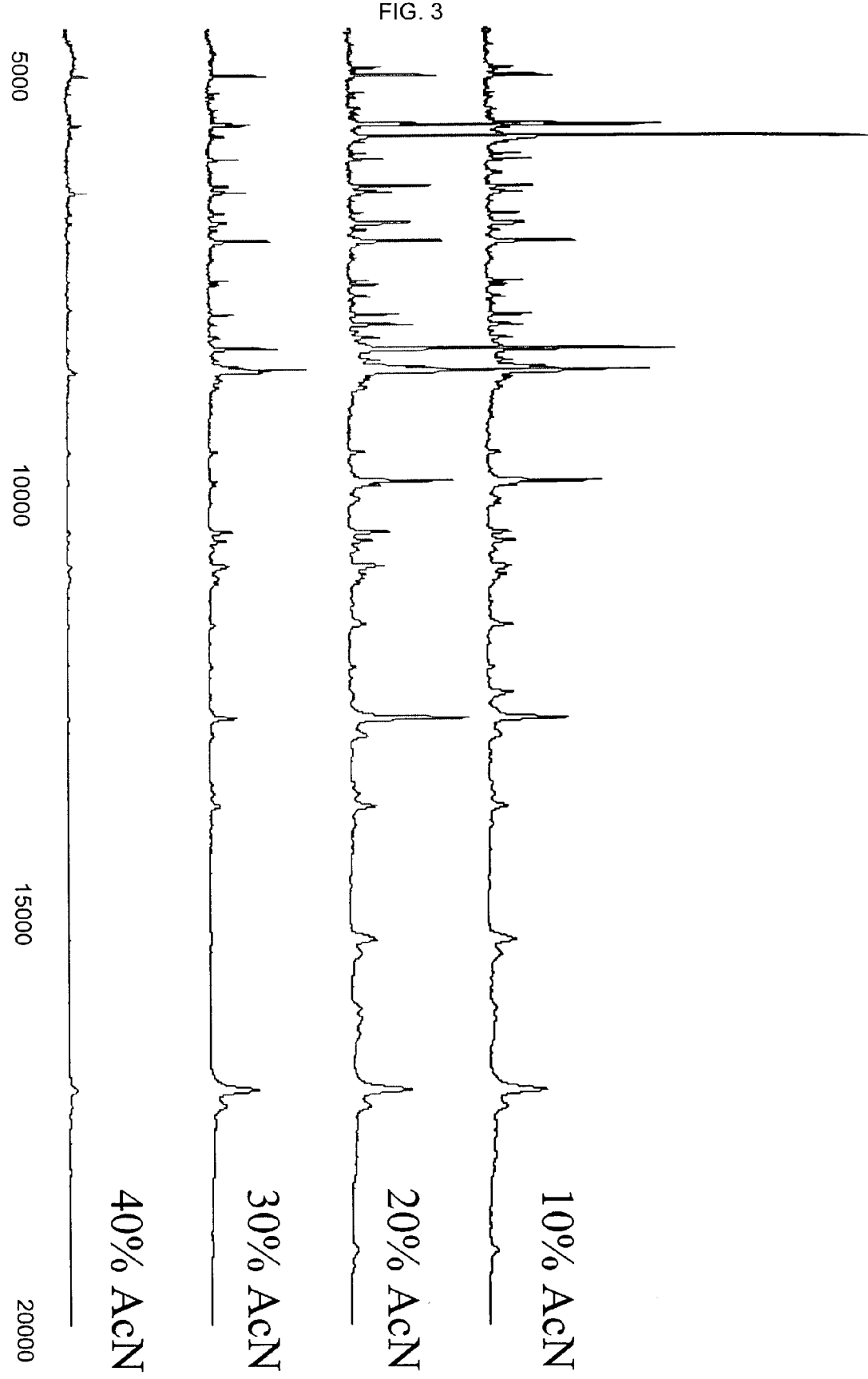
FIG. 3 is a mass spectrum of rat brain dodecyl maltoside extract adsorbed onto a chip of the invention: (A) 10% acetonitrile; (B) 20% acetonitrile; (C) 30% acetonitrile; and (D) 40% acetonitrile.

Calf Serum Sample: FIG. 3.

The results demonstrate that certain less hydrophobic proteins adsorbed onto the chip are removed by washing with increasing concentrations of acetonitrile.

EXAMPLE 4

Example 4 provides a comparison of H50 with H4.

The same protocol as Example 2 is used with H4 and H50 except using 10% acetonitrile in 1% aqueous TFA as binding and washing buffer.

Figure 4:
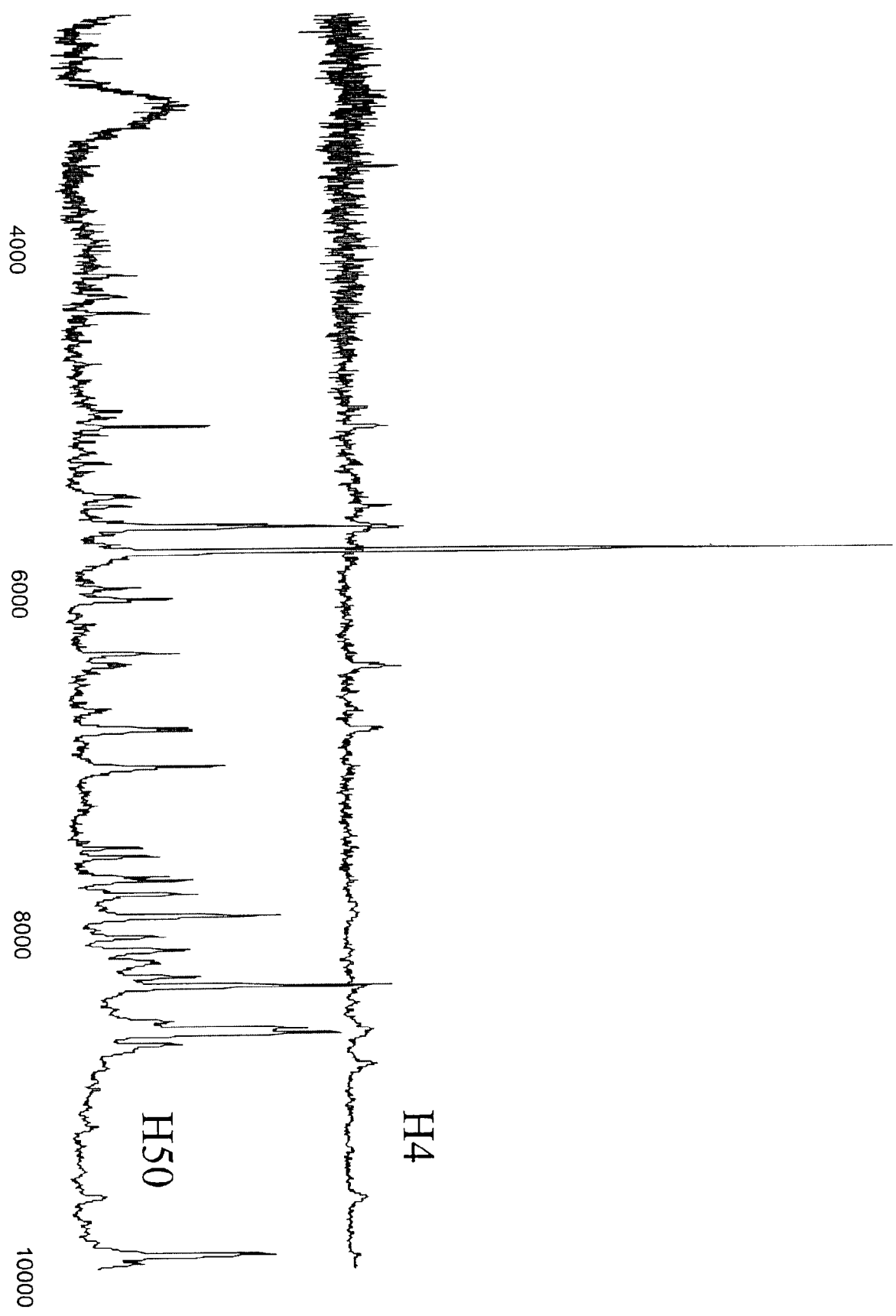
FIG. 4 is a comparison of mass spectra of an extract of rat brain adsorbed onto two different chips of the invention following a 10% acetonitrile: (A) sample adsorbed onto H4; and (B) adsorbed onto H50.
Figure 5:
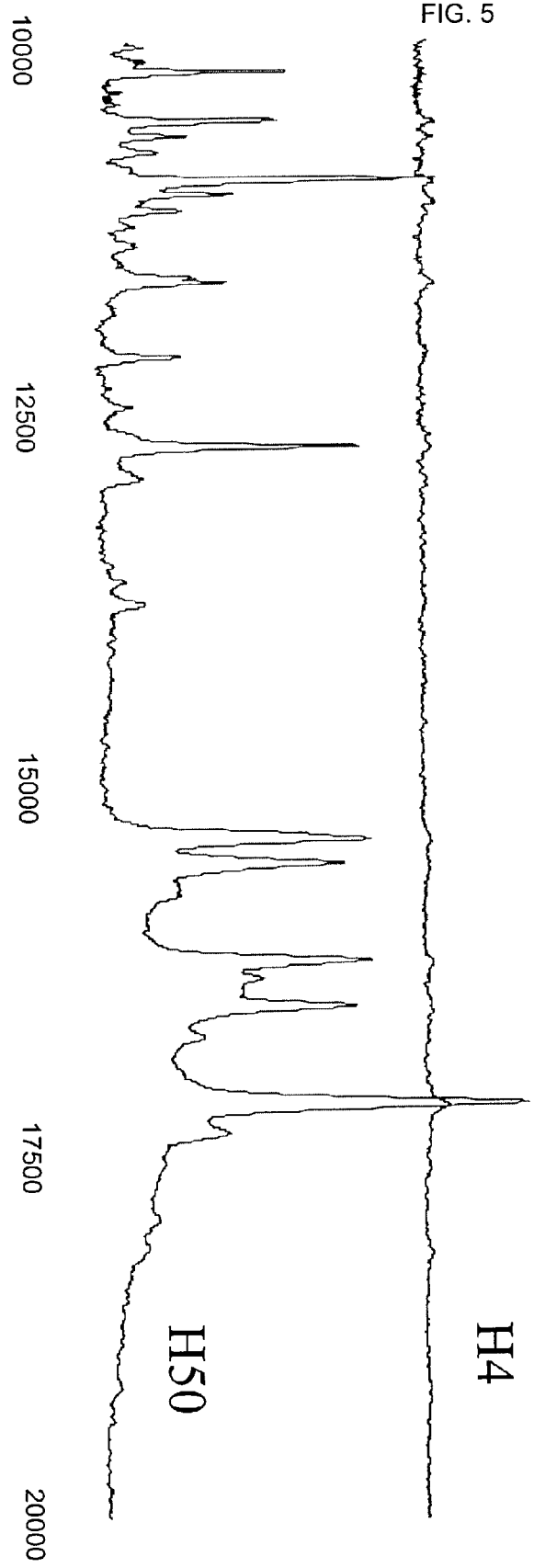
FIG. 5 is a comparison of mass spectra of an extract of rat brain adsorbed onto two different chips of the invention and washed with 5% acetonitrile: (A) adsorbed onto H4; and (B) adsorbed onto H50.
Figure 6:
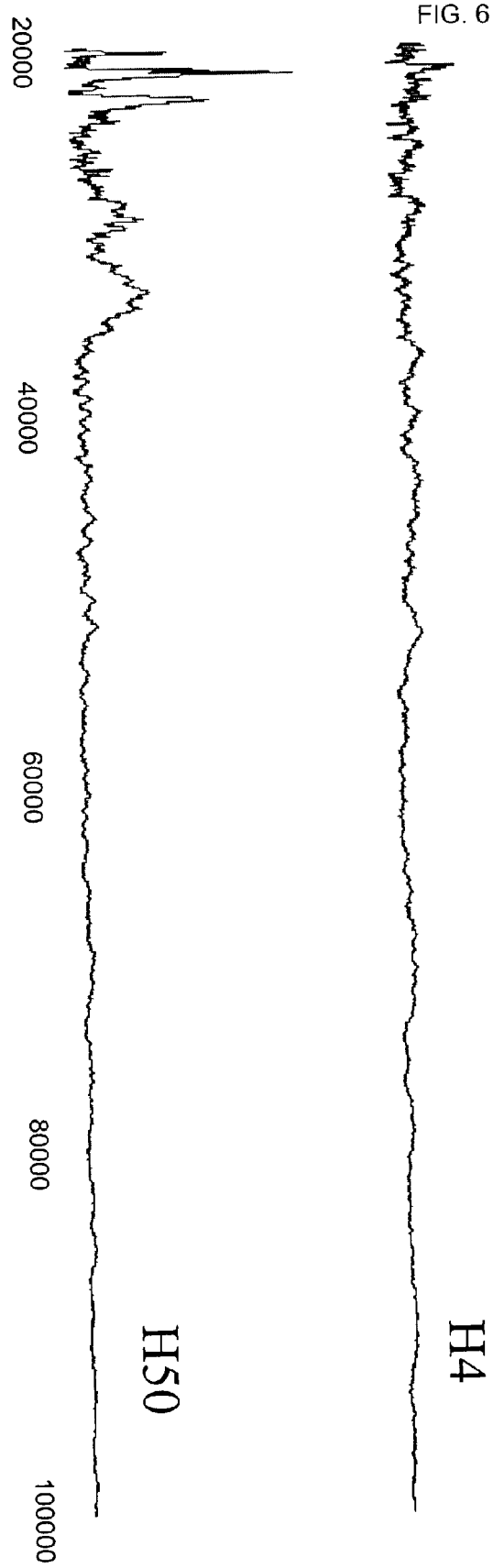
FIG. 6 is a comparison of mass spectra of an extract of rat brain adsorbed onto two different chips of the invention and washed with 10% acetonitrile: (A) adsorbed onto H4; and (B) adsorbed onto H50.

Rat Brain Sample: FIG. 4, FIG. 5, and FIG. 6 by Mass Range

Figure 7:
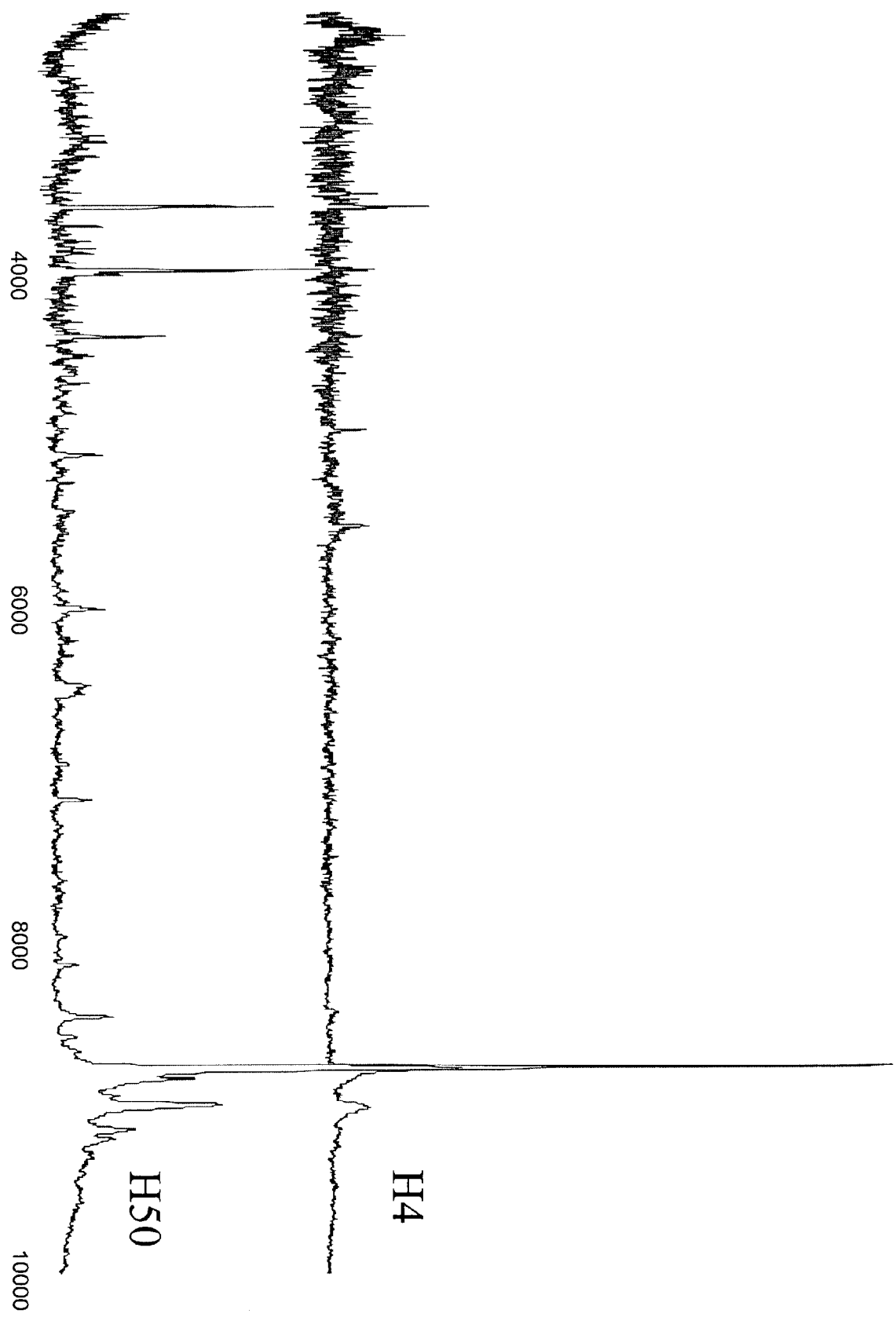
FIG. 7 is a comparison of mass spectra between about m/z 3000 and 10,000 of calf serum adsorbed onto two different chips and washed with 10% acetonitrile: (A) adsorbed onto H4; and (B) adsorbed onto C9.
Figure 8:
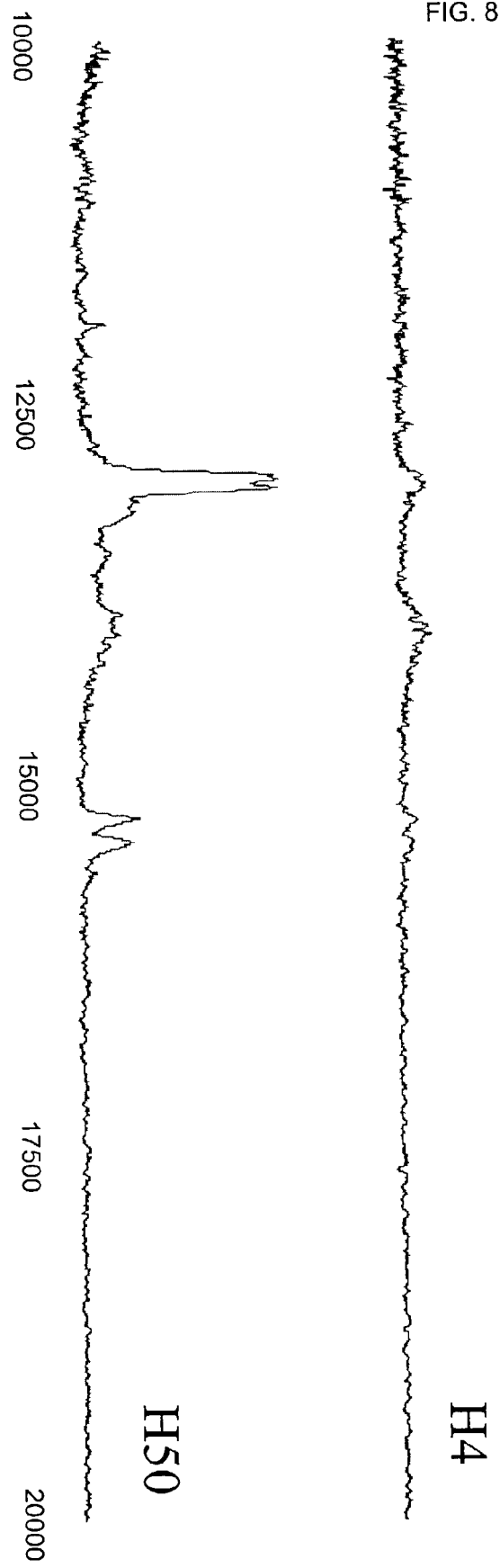
FIG. 8 is a comparison of mass spectra of calf serum adsorbed onto two different chips and washed with 10% acetonitrile: (A) adsorbed onto H4; and (B) adsorbed onto H50.
Figure 9:
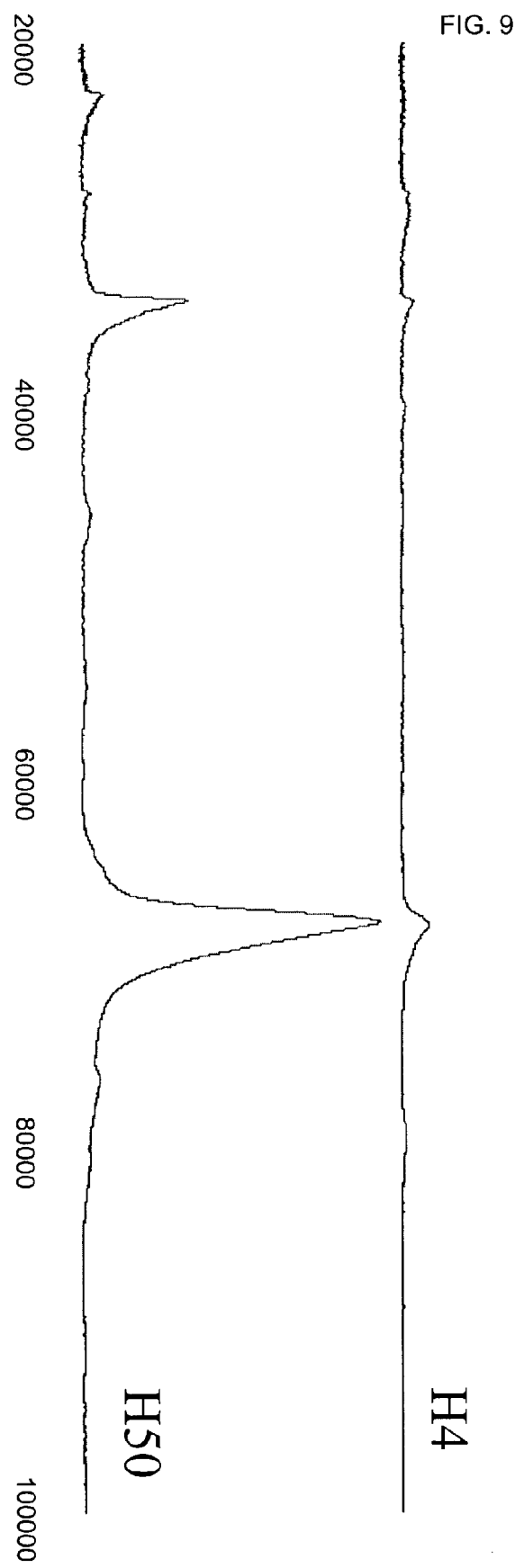
FIG. 9 is a comparison of mass spectra between about m/z 20,000 and 100,000 of calf serum adsorbed onto two different chips and washed with 10% acetonitrile: (A) adsorbed onto H4; and (B) adsorbed onto C9.

Calf Serum Sample: FIG. 7, FIG. 8, and FIG. 9 by Mass Range

The results demonstrate that certain less hydrophobic proteins adsorbed onto the H4 chip are removed more readily than those adsorbed onto the H50 chip by washing with acetonitrile.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. An adsorbent chip comprising:
   (a) a silicon dioxide coated metal substrate comprising a surface; and
   (b) an adsorbent layer attached to the surface, wherein the absorbent layer comprises a hydrogel comprising hydrophobic moieties and hydrophilic moieties wherein said hydrogel is formed by co-polymerization of a cross-linking agent and a monomer comprising a nonylphenoxy-poly(oxyethylene), wherein the hydrogel is water-swellable and binds an analyte through a salt-independent hydrophobic attraction.

2. The chip according to claim 1, wherein a unit weight of said adsorbent layer absorbs water in an amount from about 10-times to about 100-times said unit weight.

3. An adsorbent chip comprising:
   (a) a silicon dioxide coated metal substrate comprising a surface; and
   (b) an adsorbent layer attached to the surface, wherein the absorbent layer comprises a hydrogel comprising hydrophobic moieties and hydrophilic moieties, wherein said hydrogel is formed by co-polymerization of poly(ethylene glycol) dimethacrylate and a monomer having the formula:

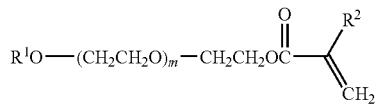

$R^1$ is nonylphenoxy;
$R^2$ is $CH_3$;
m is an integer from 2 to 100; and wherein the hydrogel is water-swellable and binds an analyte through a salt-independent hydrophobic attraction.

4. The chip of claim 3, wherein said analyte is a biomolecule.

5. The chip of claim 4, wherein said biomolecule is a polypeptide.

6. The chip of claim 3, wherein said surface further comprises an anchor moiety attaching said adsorbent layer to said surface through a covalent bond.

7. The chip of claim 6, wherein said anchor moiety comprises a silane selected from styrylethyltrimethoxysilane, styrylethylmethyldimethoxysilane, styrylethyldimethylmethoxysilane, styrylethyltrichlorosilane, (3-acryloxypropyl)trimethoxysilane, (3-acryloxypropyl)methyldimethoxysilane, (3-acryloxypropyl)dimethylmethoxysilane, (3-acryloxypropyl)trichlorosilane, (3-acryloxypropypmethyldichlorosilane, (3-acryloxypropyl)dimethylchlorosilane, (3-methacryloxypropyl)trimethoxysilane, (3-methacryloxypropyl)methyldimethoxysilane, (3-methacryloxypropyl)dimethylmethoxysilane, (3-methacryloxypropyl)trichlorosilane, (3-methacryloxypropyl)methyldichlorosilane, (3-methacryloxypropyl)dimethylchlorosilane and combinations thereof.

8. The chip of claim 3, wherein a unit weight of said adsorbent layer absorbs water in an amount from about 10-times to about 100-times said unit weight.

9. The chip of claim 3, wherein said surface comprises at least one addressable feature, said at least one addressable feature having said adsorbent layer attached thereto.

10. The chip of claim 3, wherein said surface is selected from the group consisting of rough surfaces, substantially smooth surfaces, patterned surfaces and combinations thereof.

11. The chip of claim 3, further comprising said analyte interacting hydrophobically with said adsorbent layer.

* * * * *